(12) United States Patent
Small et al.

(10) Patent No.: US 7,994,376 B2
(45) Date of Patent: Aug. 9, 2011

(54) OLEFIN OLIGOMERIZATION

(75) Inventors: Brooke L. Small, Kingwood, TX (US); Bruce E. Kreischer, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 247 days.

(21) Appl. No.: 12/480,384

(22) Filed: Jun. 8, 2009

(65) Prior Publication Data
US 2009/0270567 A1 Oct. 29, 2009

Related U.S. Application Data

(62) Division of application No. 10/782,554, filed on Feb. 19, 2004, now abandoned.

(51) Int. Cl.
C07C 2/30 (2006.01)
(52) U.S. Cl. ......... 585/530; 585/510; 585/511; 585/513
(58) Field of Classification Search .................. None
See application file for complete search history.

(56) References Cited

U.S. PATENT DOCUMENTS

| | | | |
|---|---|---|---|
| 3,635,869 A | 1/1972 | Steele et al. | |
| 3,657,298 A * | 4/1972 | King et al. | ............ 556/22 |
| 3,819,746 A | 6/1974 | Katzakian, Jr. et al. | |
| 3,873,602 A | 3/1975 | Katzakian, Jr. et al. | |
| 3,932,285 A | 1/1976 | Ceprini et al. | |
| 3,962,182 A | 6/1976 | Steele et al. | |
| 3,968,135 A | 7/1976 | Steele et al. | |
| 3,977,996 A | 8/1976 | Katzakian, Jr. et al. | |
| 3,978,026 A | 8/1976 | Katzakian, Jr. et al. | |
| 4,017,429 A | 4/1977 | Steele et al. | |
| 4,057,565 A | 11/1977 | Manzer | |
| 4,451,573 A | 5/1984 | Ikegami et al. | |
| 4,668,838 A | 5/1987 | Briggs | |
| 4,777,315 A | 10/1988 | Levine et al. | |
| 4,853,356 A | 8/1989 | Briggs | |
| 4,876,229 A | 10/1989 | Furtek | |
| 4,971,986 A | 11/1990 | Stanek et al. | |
| 5,081,089 A | 1/1992 | Rekers et al. | |
| 5,118,648 A | 6/1992 | Furtek et al. | |
| 5,137,994 A | 8/1992 | Goode et al. | |
| 5,198,401 A | 3/1993 | Turner et al. | |
| 5,198,563 A | 3/1993 | Reagen et al. | |
| 5,288,823 A | 2/1994 | Reagan et al. | |
| 5,331,070 A | 7/1994 | Pettijohn et al. | |
| 5,331,104 A | 7/1994 | Reagen et al. | |
| 5,340,785 A | 8/1994 | Reagen et al. | |
| 5,340,892 A | 8/1994 | Kuramoto | |
| 5,360,879 A | 11/1994 | Reagen et al. | |
| 5,376,612 A | 12/1994 | Reagen et al. | |
| 5,382,738 A | 1/1995 | Reagen et al. | |
| 5,393,719 A | 2/1995 | Pettijohn et al. | |
| 5,399,539 A | 3/1995 | Reagen et al. | |
| 5,438,027 A | 8/1995 | Reagen et al. | |
| 5,451,645 A | 9/1995 | Reagen et al. | |
| 5,470,926 A | 11/1995 | Reagen et al. | |
| 5,491,272 A | 2/1996 | Tanaka et al. | |
| 5,523,507 A | 6/1996 | Reagen et al. | |
| 5,543,375 A | 8/1996 | Lashier et al. | |
| 5,550,305 A | 8/1996 | Wu | |
| 5,557,026 A | 9/1996 | Tanaka et al. | |
| 5,563,312 A | 10/1996 | Knudsen et al. | |
| 5,689,028 A | 11/1997 | Lashier et al. | |
| 5,696,240 A | 12/1997 | Vallarino et al. | |
| 5,714,556 A | 2/1998 | Johnson et al. | |
| 5,731,487 A | 3/1998 | Tamura et al. | |
| 5,744,677 A | 4/1998 | Wu | |
| 5,750,816 A | 5/1998 | Araki et al. | |
| 5,750,817 A | 5/1998 | Tanaka et al. | |
| 5,763,723 A | 6/1998 | Reagen et al. | |
| 5,786,291 A | 7/1998 | Speca et al. | |
| 5,786,431 A | 7/1998 | Reagen et al. | |
| 5,811,618 A | 9/1998 | Wu | |
| 5,814,575 A | 9/1998 | Reagen et al. | |
| 5,830,955 A | 11/1998 | Takeda et al. | |
| 5,856,257 A | 1/1999 | Freeman et al. | |
| 5,856,610 A | 1/1999 | Tamura et al. | |
| 5,856,612 A | 1/1999 | Araki et al. | |
| 5,859,303 A | 1/1999 | Lashier | |

(Continued)

FOREIGN PATENT DOCUMENTS

AU 650808 6/1994

(Continued)

OTHER PUBLICATIONS

Adams, Harry, et al., Complexes of ligands providing endogenous bridges. Part 1. The syntheses and crystal structures of barium and lead(II) complexes of macrocyclic schiff bases derived from heterocyclic dicarbonyls and 1,n-diamino-n'-hydroxyalkanes (n,n' = 3,2; 4,2; or 5,3), J. Chem. Soc. Dalton Trans., 1987, Iss. 1, pp. 207-218., XP009070491.

(Continued)

Primary Examiner — Tam M Nguyen
(74) Attorney, Agent, or Firm — Conley Rose, P.C.; Rodney B. Carroll; Lynda S. Jolly

(57) ABSTRACT

Provided is a method of oligomerizing alpha olefins. In an embodiment, an oligomerization catalyst system is contacted in at least one continuous reactor with a feed comprising olefins; an effluent comprising product olefins having at least four carbon atoms is withdrawn from the reactor; the oligomerization catalyst system comprises iron or cobalt, or combinations thereof; and the single pass conversion of ethylene is at least about 40 weight percent among product olefins having at least four carbon atoms. In another embodiment, the single pass conversion of ethylene comprises at least about 65 weight percent among product olefins having at least four carbon atoms. In another embodiment, product olefins of the effluent having twelve carbon atoms comprise at least about 95 weight percent 1-dodecene. In another embodiment, product olefins comprise at least about 80 weight percent linear 1-alkenes. In another embodiment, product olefins comprise at least about 20 weight percent alpha olefins having from about 8 to about 20 carbon atoms. In another embodiment, the oligomerization catalyst system provided comprises a selective 1-hexene (S1H) catalyst.

34 Claims, 5 Drawing Sheets

U.S. PATENT DOCUMENTS

| | | |
|---|---|---|
| 5,910,619 A | 6/1999 | Urata et al. |
| 5,919,996 A | 7/1999 | Freeman et al. |
| 5,955,555 A | 9/1999 | Bennett |
| 5,968,866 A | 10/1999 | Wu |
| 5,986,153 A | 11/1999 | Kallenbach et al. |
| 6,031,145 A | 2/2000 | Commereuc et al. |
| 6,063,881 A | 5/2000 | Bennett |
| 6,103,654 A | 8/2000 | Commereuc et al. |
| 6,103,658 A | 8/2000 | Mackenzie et al. |
| 6,103,946 A | 8/2000 | Brookhart, III et al. |
| 6,127,301 A | 10/2000 | Iwanaga et al. |
| 6,133,495 A | 10/2000 | Urata et al. |
| 6,150,482 A | 11/2000 | Brookhart et al. |
| 6,214,761 B1 | 4/2001 | Bennett |
| 6,221,986 B1 | 4/2001 | Commereuc et al. |
| 6,239,237 B1 | 5/2001 | Xu et al. |
| 6,281,303 B1 | 8/2001 | Lavoie et al. |
| 6,291,733 B1 | 9/2001 | Small et al. |
| 6,337,297 B1 | 1/2002 | Mimura et al. |
| 6,344,594 B1 | 2/2002 | Sen et al. |
| 6,369,177 B1 | 4/2002 | Tohi et al. |
| 6,380,451 B1 | 4/2002 | Kreischer et al. |
| 6,399,535 B1 | 6/2002 | Shih et al. |
| 6,414,098 B1 | 7/2002 | Engehausen et al. |
| 6,417,305 B2 | 7/2002 | Bennett |
| 6,417,364 B1 | 7/2002 | Lenges |
| 6,423,848 B2 | 7/2002 | Bennett |
| 6,451,939 B1 | 9/2002 | Britovsek et al. |
| 6,455,648 B1 | 9/2002 | Freeman et al. |
| 6,458,739 B1 | 10/2002 | Kimberley et al. |
| 6,458,905 B1 | 10/2002 | Schmidt et al. |
| 6,461,994 B1 | 10/2002 | Gibson et al. |
| 6,465,386 B1 | 10/2002 | Maddox et al. |
| 6,489,497 B1 | 12/2002 | Brookhart, III et al. |
| 6,521,806 B1 | 2/2003 | Tamura et al. |
| 6,534,691 B2 | 3/2003 | Culver et al. |
| 6,545,108 B1 | 4/2003 | Moody et al. |
| 6,548,672 B1 | 4/2003 | Gibson et al. |
| 6,555,633 B1 | 4/2003 | Tanaka et al. |
| 6,555,723 B2 | 4/2003 | Schiffino |
| 6,562,973 B1 | 5/2003 | Liu |
| 6,683,187 B2 | 1/2004 | De Boer et al. |
| 6,689,848 B2 | 2/2004 | Nagy et al. |
| 6,710,006 B2 | 3/2004 | De Boer et al. |
| 6,740,715 B2 | 5/2004 | Brookhart, III et al. |
| 6,777,584 B2 | 8/2004 | Patil et al. |
| 6,828,269 B2 | 12/2004 | Commereuc et al. |
| 6,841,693 B1 | 1/2005 | Watanabe et al. |
| 6,844,290 B1 | 1/2005 | Maas et al. |
| 6,900,152 B2 | 5/2005 | Yoshida et al. |
| 6,903,042 B2 | 6/2005 | Drochon et al. |
| 6,911,505 B2 | 6/2005 | Small |
| 6,911,506 B2 | 6/2005 | Small et al. |
| 6,927,313 B2 | 8/2005 | Bianchini et al. |
| 7,001,964 B2 | 2/2006 | Small |
| 7,037,988 B2 | 5/2006 | De Boer et al. |
| 7,045,632 B2 | 5/2006 | Small |
| 7,049,442 B2 | 5/2006 | De Boer et al. |
| 7,053,259 B2 | 5/2006 | Culver et al. |
| 7,129,304 B1 | 10/2006 | Small et al. |
| 7,176,266 B2 | 2/2007 | Sato et al. |
| 7,179,871 B2 | 2/2007 | De Boer et al. |
| 7,223,893 B2 | 5/2007 | Small et al. |
| 7,238,764 B2 | 7/2007 | De Boer et al. |
| 7,268,096 B2 | 9/2007 | Small et al. |
| 7,271,121 B2 | 9/2007 | Small et al. |
| 7,297,806 B2 | 11/2007 | Brookhart, III et al. |
| 7,304,159 B2 | 12/2007 | De Boer et al. |
| 7,384,886 B2 | 6/2008 | Knudsen et al. |
| 7,442,819 B2 | 10/2008 | Ionkin et al. |
| 7,456,284 B2 | 11/2008 | Small |
| 7,589,245 B2 | 9/2009 | De Boer et al. |
| 2001/0053742 A1 | 12/2001 | Knudsen et al. |
| 2004/0116758 A1 | 6/2004 | De Boer et al. |
| 2004/0122269 A1 | 6/2004 | Van Zon et al. |
| 2004/0122271 A1 | 6/2004 | Van Zon et al. |
| 2005/0187098 A1 | 8/2005 | Knudsen et al. |
| 2005/0187418 A1 | 8/2005 | Small et al. |
| 2007/0043181 A1 | 2/2007 | Knudsen et al. |
| 2007/0112150 A1 | 5/2007 | Small et al. |
| 2008/0058534 A1 | 3/2008 | Knudsen et al. |
| 2008/0177122 A1 | 7/2008 | Knudsen et al. |
| 2009/0163755 A1 | 6/2009 | Small |
| 2009/0292090 A1 | 11/2009 | Knudsen et al. |

FOREIGN PATENT DOCUMENTS

| | | | |
|---|---|---|---|
| CA | 2087578 | A1 | 7/1994 |
| CA | 2396614 | A1 | 7/2001 |
| CA | 2115639 | C | 10/2004 |
| CN | 1256968 | A | 6/2000 |
| CN | 1294109 | A | 5/2001 |
| CN | 1306014 | A | 8/2001 |
| CN | 1358772 | A | 7/2002 |
| CN | 1361093 | A | 7/2002 |
| CN | 1374281 | A | 10/2002 |
| CN | 1850339 | A | 10/2006 |
| EP | 0416815 | A2 | 3/1991 |
| EP | 0537609 | A2 | 4/1993 |
| EP | 0608447 | A1 | 8/1994 |
| EP | 0668105 | A2 | 8/1995 |
| EP | 1110930 | A1 | 6/2001 |
| EP | 1188762 | A1 | 3/2002 |
| EP | 1229020 | A1 | 8/2002 |
| EP | 1325924 | A1 | 7/2003 |
| FR | 2833191 | A | 6/2003 |
| FR | 2857964 | A1 | 1/2005 |
| JP | 6263822 | | 9/1994 |
| JP | 7010780 | | 1/1995 |
| JP | 7017878 | | 1/1995 |
| JP | 7018013 | | 1/1995 |
| JP | 7118173 | | 5/1995 |
| JP | 7118174 | | 5/1995 |
| JP | 7118175 | | 5/1995 |
| JP | 7118324 | | 5/1995 |
| JP | 7118325 | | 5/1995 |
| JP | 7118326 | | 5/1995 |
| JP | 7118327 | | 5/1995 |
| JP | 7118328 | | 5/1995 |
| JP | 7149671 | | 6/1995 |
| JP | 7149672 | | 6/1995 |
| JP | 7149673 | | 6/1995 |
| JP | 7149674 | | 6/1995 |
| JP | 7149675 | | 6/1995 |
| JP | 7149676 | | 6/1995 |
| JP | 7149677 | | 6/1995 |
| JP | 7157512 | | 6/1995 |
| JP | 7215896 | | 8/1995 |
| JP | 8059732 | | 3/1996 |
| JP | 8134131 | | 5/1996 |
| JP | 8151409 | | 6/1996 |
| JP | 8183747 | | 7/1996 |
| JP | 8239330 | | 9/1996 |
| JP | 8239331 | | 9/1996 |
| JP | 8239418 | | 9/1996 |
| JP | 8245429 | | 9/1996 |
| JP | 8245430 | | 9/1996 |
| JP | 8245431 | | 9/1996 |
| JP | 8283330 | | 10/1996 |
| JP | 8283332 | | 10/1996 |
| JP | 8301921 | | 11/1996 |
| JP | 8301922 | | 11/1996 |
| JP | 8301923 | | 11/1996 |
| JP | 8301924 | | 11/1996 |
| JP | 8301925 | | 11/1996 |
| JP | 8325317 | | 12/1996 |
| JP | 8325318 | | 12/1996 |
| JP | 8325319 | | 12/1996 |
| JP | 8333407 | | 12/1996 |
| JP | 9012627 | | 1/1997 |
| JP | 9020692 | | 1/1997 |
| JP | 9020693 | | 1/1997 |
| JP | 9040710 | | 2/1997 |
| JP | 9087318 | | 3/1997 |
| JP | 9143213 | | 6/1997 |
| JP | 9176228 | | 7/1997 |
| JP | 9176229 | | 7/1997 |
| JP | 9188634 | | 7/1997 |
| JP | 9194400 | | 7/1997 |
| JP | 9194524 | | 7/1997 |

| | | |
|---|---|---|
| JP | 9262480 | 10/1997 |
| JP | 9268133 | 10/1997 |
| JP | 9268134 | 10/1997 |
| JP | 9268135 | 10/1997 |
| JP | 10007593 | 1/1998 |
| JP | 10007594 | 1/1998 |
| JP | 10007595 | 1/1998 |
| JP | 10007681 | 1/1998 |
| JP | 10036431 | 2/1998 |
| JP | 10036432 | 2/1998 |
| JP | 10036433 | 2/1998 |
| JP | 10036435 | 2/1998 |
| JP | 10045634 | 2/1998 |
| JP | 10045638 | 2/1998 |
| JP | 10045833 | 2/1998 |
| JP | 10060043 | 3/1998 |
| JP | 10087517 | 4/1998 |
| JP | 10087518 | 4/1998 |
| JP | 10101587 | 4/1998 |
| JP | 10218799 | 8/1998 |
| JP | 11060511 | 3/1999 |
| JP | 11060626 | 3/1999 |
| JP | 11092407 | 4/1999 |
| JP | 11092408 | 4/1999 |
| JP | 2000176291 | 6/2000 |
| JP | 2000202299 | 7/2000 |
| JP | 2000212212 | 8/2000 |
| JP | 2001002724 | 1/2001 |
| JP | 2001009290 | 1/2001 |
| JP | 2001096164 | 4/2001 |
| JP | 2001149788 | 6/2001 |
| JP | 2001187345 | 7/2001 |
| JP | 2002045703 | 2/2002 |
| JP | 2002066329 | 3/2002 |
| JP | 2002102710 | 4/2002 |
| JP | 2002172327 | 6/2002 |
| JP | 2002200429 | 7/2002 |
| JP | 2002205960 | 7/2002 |
| JP | 2002233764 | 8/2002 |
| JP | 2002233765 | 8/2002 |
| JP | 2003071294 | 3/2003 |
| JP | 2003088760 | 3/2003 |
| JP | 2004136270 | 5/2004 |
| JP | 2004136271 | 5/2004 |
| JP | 2004306014 | 11/2004 |
| KR | 20030029253 | 4/2003 |
| WO | 9415940 A1 | 7/1994 |
| WO | 9623010 A2 | 8/1996 |
| WO | 9827124 A1 | 6/1998 |
| WO | 9919280 A1 | 4/1999 |
| WO | 9962963 A1 | 12/1999 |
| WO | 9962967 A2 | 12/1999 |
| WO | 0020427 A1 | 4/2000 |
| WO | 0037175 A1 | 6/2000 |
| WO | 0068280 A1 | 11/2000 |
| WO | 0069923 A1 | 11/2000 |
| WO | 0110875 A1 | 2/2001 |
| WO | 0136379 A1 | 5/2001 |
| WO | 0136503 A1 | 5/2001 |
| WO | 0138270 A1 | 5/2001 |
| WO | 0147839 A1 | 7/2001 |
| WO | 0148028 A1 | 7/2001 |
| WO | 0158874 A1 | 8/2001 |
| WO | 0168572 A1 | 9/2001 |
| WO | 0168725 A2 | 9/2001 |
| WO | 0174830 A1 | 10/2001 |
| WO | 0183447 A2 | 11/2001 |
| WO | 0200339 A2 | 1/2002 |
| WO | 0204119 A1 | 1/2002 |
| WO | 0210133 A1 | 2/2002 |
| WO | 0228805 A2 | 4/2002 |
| WO | 0234701 A1 | 5/2002 |
| WO | 02066404 A1 | 8/2002 |
| WO | 02066405 A1 | 8/2002 |
| WO | 02079276 A2 | 10/2002 |
| WO | 02083306 A2 | 10/2002 |
| WO | 02083306 A3 | 10/2002 |
| WO | 0296919 A1 | 12/2002 |
| WO | 03004158 A2 | 1/2003 |
| WO | 03011876 A1 | 2/2003 |
| WO | 03024902 A1 | 3/2003 |
| WO | 03053890 A1 | 7/2003 |
| WO | 03053891 A1 | 7/2003 |
| WO | 03059511 A1 | 7/2003 |
| WO | 2004043887 A2 | 5/2004 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2004078799 A1 | 9/2004 |
| WO | 2005082816 A1 | 9/2005 |
| WO | 2005092821 A1 | 10/2005 |
| WO | 2005111099 A1 | 11/2005 |
| WO | 2006008438 A1 | 1/2006 |
| WO | 2006016101 A1 | 2/2006 |
| WO | 2007021955 A2 | 2/2007 |
| WO | 2007024504 A1 | 3/2007 |
| WO | 2007059015 A1 | 5/2007 |
| WO | 2007080081 A2 | 7/2007 |
| WO | 2008038173 A2 | 4/2008 |
| WO | 2009085411 A1 | 7/2009 |

OTHER PUBLICATIONS

Agapie, Theodor, et al., "Mechanistic Studies of the Ethylene Trimerization Reaction with Chromium-Diphosphine Catalysts: Experimental Evidence for a Mechanism Involving Metallacyclic Intermediates," JACS Communications, J. Am. Chem. Soc., vol. 126, No. 5, 2004, pp. 1304-1305.

Agapie, Theodor, et al., "Structural and mechanistic studies of a chromium-diphosphine system for catalytic trimerization of ethylene," INOR 494, 227th ACS National Meeting, Anaheim, CA Mar. 28-Apr. 1, 2004, 1 pg.

"Aldrich", Catalog Handbook of Fine Chemicals, Aldrich Chemical Company, 1990-1991, Cover page, Information sheet & pp. 1274-1275.

Allen, Geoffrey, Editor, "Comprehensive polymer science, vol. 4," 1989, pp. 1-108, 409-412, 533-584 plus 1 cover page, 2 publishing pages, and 2 contents pages, Pergamon Press, England.

Alobaidi, Fahad, et al., "Direct Synthesis of Linear Low-Density Polyethylene of Ethylene/1-Hexene from Ethylene with a Tandem Catalytic System in a Single Reactor," Journal of Polymer Science: Part A: Polymer Chemistry, vol. 42, 2004, pp. 4327-4336.

Andes, Cecily, et al., "Formation of an Ethene Trimerization Catalyst from (CH3)TACL3," INOR 261, 1 page.

Andes, Cecily, et al., "New Tantalum Catalyst for the Selective Trimerization of Ethene," INOR 273, 1 pg.

Andes, Cecily, et al., "New Tantalum-Based Catalyst System for the Selective Trimerization of Ethene to 1-Hexene," J. Am. Chem. Soc., vol. 123, No. 30, 2001, pp. 7423-7424.

Blok, Arno NJ., et al, "Mechanism of Ethene Trimerization at an ansa-(Arene)(cyclopentadienyl) Titanium Fragment," Organometallics, vol. 22, No. 13, 2003, pp. 2564-2570.

Bollmann, Annette, et al., "Ethylene Tetramerization: A New Route to Produce 1-Octene in Exceptionally High Selectivities," JACS Communications, J. Am. Chem. Soc., vol. 126, No. 45, 2004, pp. 14712-14713.

Boor, Jr., John, "Ziegler-natta catalysts and polymerizations,"1979, 1 cover page and 1 publishing page, Academic Press, Inc., New York.

Briggs, John, "The Selective Trimerization of Ethylene to Hex-1-ene," J. Chem. Soc., Chem Commun., 1989, pp. 674-675.

Brintzinger, Hans H., et al., "Stereospecific olefin polymerization with chiral metallocene catalysts," Angew. Chem. Int. Ed. Engl., 1995, pp. 1143-1170, VCH Verlagsgesellschaft mbH, Weinheim.

Britovsek, George J. P., et al., "Oligomerisation of ethylene by bis(imino)pyridyliron and -cobalt complexes," Chem. Eur. J., 2000, pp. 2221-2231, vol. 6, No. 12. WILEY-VCH Verlag GmbH, Weinheim.

Carter, Anthea, et al., "High activity ethylene trimerisation catalysts based on diphosphine ligands,"Chem. Commun., 2002, pp. 858•859.

Chen, Jwu-Ting, et al., "Dimerization and Oligomerization of Ethylene Catalyzed by a Palladium(II) Complex with Iminephosphine Ligand," J. Chin. Chem. Soc., vol. 47, No. 1, 2000, pp. 279-281.

Dai Changhua, "Commercialization of 1-Hexene by Ethylene Trimerization in China," Petroleum & Petrochemical Today, vol. 10, No. 17, 2002, pp. 25-29.

De Bruin, Theodorus J.M., et al., "Hemilabile Ligand Induced Selectivity: a DFT Study on Ethylene Trimerization Catalyzed by Titanium Complexes," Organometallics, vol. 22, No. 17, 2003, pp. 3404-3413.

De Wet-Roos, Deon, et al., "Homogeneous Tandem Catalysis of Bis(2-decylthioethyl)amine-Chromium Trimerization Catalyst in Combination with Metallocene Catalysts," Macromolecules, vol. 37, No. 25, 2004, pp. 9314-9320.

Deckers, Patrick J.W., et al., "Catalytic Trimerization of Ethene with Highly Active Cyclopentadienyl-Arene Titanium Catalysts," Organometallics, vol. 21, No. 23, 2002, pp. 5122-5135.

Deckers, Patrick J.W., et al., "Switching a Catalyst System from Ethene Polymerization to Ethene Trimerization with a Hemilabile Ancillary Ligand," Angew. Chem. Int. Ed., vol. 40, No. 13, 2001, pp. 2516-2519.

Dixon, John T., et al., "Advances in Selective Ethylene Trimerisation—A Critical Overview," Journal of Organometallic Chemistry, vol. 689, 2004, pp. 3641-3668.

Emrich, Rainer, et al., "The Role of Metallacycles in the Chromium-Catalyzed Trimerization of Ethylene," Organometallics, vol. 16, No. 8, Apr. 15, 1997, pp. 1511-1513.

Fang, Yiqun, et al., "A new chromium-based catalyst coated with paraffin for ethylene oligomerization and the effect of chromium state on oligomerization selectivity," Applied Cataysis A: General, vol. 235, 2002, pp. 33-38.

Foreign communication from a related counterpart application—International Search Report and Written Opinion, PCT/US2004/004472, Jul. 16, 2004, 7 pages.

Foreign communication from a related counterpart application—International Search Report and Written Opinion, PCT/US2005/005416; Jun. 1, 2005, 10 pages.

Foreign communication from a related counterpart application—International Search Report and Written Opinion, PCT/US2005/005437, Jul. 4, 2005, 13 pgs.

Foreign communication from a related counterpart application—International Search Report and Written Opinion, PCT/US2005/042175, Aug. 17, 2006, 9 pages.

Foreign communication from a related counterpart application—International Preliminary Report on Patentability, PCT/US2005/005416, Aug. 22, 2006, 6 pages.

Foreign communication from a related counterpart application—International Search Report and Written Opinion, PCT/US2006/031303, Dec. 19, 2006, 13 pgs.

Foreign communication from a counterpart application—Written Opinion, SG 200625612-1, Aug. 28, 2007, 5 pages.

Foreign communication from a counterpart application, EP 05723396.7—Examination Report, Oct. 10, 2007, 4 pages.

Foreign communication from a related counterpart application—International Preliminary Report on Patentability, PCT/US2006/031303, Feb. 20, 2008, 7 pages.

Foreign communication from a counterpart application No. CA 2,556,879 filed Feb. 18, 2005—Filing of Prior Art under Section 34.1 of the Patent Act Protest under Section 10 of the Patent Rules, Jan. 11, 2008, 11 pages.

Foreign communication from a counterpart application—International Search Report and Written Opinon, PCT/US2008/083026, Mar. 19, 2009, 9 pages.

Freeman, J.W., et al., "Selective Production of 1-Hexene from Ethylene," Florida Catalysis Conference, 30 pgs., undated but admitted as prior art.

Hessen, Bart, "Monocyclopentadienyl titanium catalysts: ethane polymerisation versus ethene trimerisation," Journal of Molecular Catalysis A: Chemical, vol. 213, 2004, pp. 129-135.

Huang, Jiling, et al., "Ethylene trimerization with a half-sandwich titanium complex bearing a pendant thienyl group," Chem. Commun., 2003, pp. 2816-2817.

Jiang, Tao, et al., "Research advances of 1-hexene process by ethylene trimerization," Petrochemical Technology & Application, vol. 18, No. 5, 2000, pp. 284-287.

Kohn, R.D., "Olefin Trimerization with 1,3,5-Triazacycloltexane Complexes of Chromium,"INOR 278, Book of Abstracts, 215th ACS National Meeting, Dallas, Mar. 29-Apr. 2, 1998, 1 pg.

Kohn, Randolf D., et al., "1,3,5-Triazacyclohexane Complexes of Chromium as Homogeneous Model Systems for the Phillips Catalyst, " American Chemical Society Symposium Series, 2003, vol. 857 (Beyond Metallocenes), pp. 88-100.

Kohn, Randolf D., et al., "1,3,5-Triazacyclohexane Complexes of Chromium as Homogeneous Model Systems for the Phillips Catalyst," Organometallic Catalysts and Olefin Polymerization, pp. 147-155, undated but admitted as prior art.

Kohn, Randolf D., et al., "Selective Trimerization of a-Olefins with Triazacyclohexane Complexes of Chromium as Catalysts," Agnew. Chem. Int. Ed. vol. 39, No. 23, 2000, pp. 4337-4339.

Kumar, R. N., et al., "Mononuclear and binuclear complexes of Fe(II) and Cu(II) with 2,6-diacetyl pyridine monoxime and phenylene diamine," Jul.-Sep. 1999, pp. 964-969 plus 1 cover page, vol. 11, No. 3, Asian Journal of Chemistry.

Li, Yuesheng, et al., "Preparation of iron- or cobalt-based polynuclear pyridine-containing diimine catalysts for olefin polymerization," XP-002284349, Jun. 14, 2004, 1 page, CAPLUS.

Luo, He-Kuan, et al., "The effect of halide and the coordination geometry of chromium center in homogeneous catalyst system for ethylene trimerization," Journal of Molecular Catalysis A: Chemical, vol. 221, Elsevier, 2004, pp. 9-17.

Mahomed, Hamdani, et al., "Ethylene trimerization catalyst based on substituted cyclopentadienes," Applied Catalysis A: General, vol. 255, 2003, pp. 355-359.

Manyik, R.M., et al., "A Soluble Chromium-Based Catalyst for Ethylene Trimerization and Polymerization," Journal of Catalysis, vol. 47, 1977, pp. 197-209.

Mark, Herman, F., Editor, "Encyclopedia of polymer science and engineering," vol. 6, 1986, pp. 383-522 plus 1 cover page, 2 publishing pages, and 1 contents page, John Wiley & Sons, Inc., USA.

McGuinness, David S., et al., "First Cr(III)-SNS Complexes and Their Use as Highly Efficient Catalysts for the Trimerization of Ethylene to 1-Hexene," JACS Communications, J. Am. Chem. Soc., vol. 125, No. 18, 2003, pp. 5272-5273.

McGuinness, David S., et al., "Novel Cr-PNP complexes as catalysts for the trimerization of ethylene," J. Chem. Soc., Chem. Corrimun., 2003, pp. 334-335.

Meijboom, Nicolaas, et al., "Organometallic Chemistry of Chromium(VI): Synthesis of Chromium(VI) Alkyls and Their Precursors. X-ray Crystal Structure of the Metallacycle Cr(N'Bu)2(o-(CHSiMe3)2C6H4}," Organometallics, vol. 9, No. 3, 1990, pp. 774-782.

Mihan, Shahram, et al., "Triazacyclohexane Complexes of Chromium for Selective Trimerization," INOR 114, Abstracts of Papers-Am. Chem. Soc., 221', 2001, I pg.

Monoi, Takashi, et al., "Silica-supported Cr[N(SiMe3)2]3/isobutylalumoxane catalyst for selective ethylene trimerization," Journal of Molecular Catalysis A: Chemical, vol. 187, 2002, pp. 135-141.

Morgan, David H., et al., The Effect of Aromatic Ethers on the Trimerisation of Ethylene using a Chromium Catalyst and Aryloxy Ligands, XP-002409661, Adv. Synth. Catal., vol. 345, 2003, pp. 939-942.

Nelson, S. Martin, et al., "Metal-ion controlled reactions of 2,6-diacetylpyridine with 1,2-diaminoethane and 2,6-diformylpyridine with o-phenylenediamine and the crystal and moleular structure of a pentagonal pyramidal cadmium (II) complex containing unidentate o-phenylenediamine," 1982, pp. 407-415, J.C.S. Dalton.

Ninanalov, II., et al., "Equilibrium of the trimerization of ethylene into hexenes," Zh., Khim, 1983, Abstract No. 24B897, 2 pgs.

Ranwell, A., et at, "Potential Application of Ionic Liquids for Olefin Oligomerization," Am. Chem. Soc. Symposium Series, 818 (Ionic Liquids), 2002, pp. 147-160.

Rao, Guo-ying, et al., "Coordination mode of the Cr(2-ethylhexanoate)3/triethylalurnintimidimethylpyrrole/tetrachloroethane," Journal of Beijing University of Chemical Technology, 2003, vol. 30 , No. 1, pp. 80-82.

Reagen, W.K., "Chromium(II) and (III) Pyrrotyl Ethylene Oligomerization Catalysts Synthesis and Crystal Structure of Square Planar Cr(NC4H4)4-2, and Pentanuclear (Crs(NC.41-14)10(0C4H8)4)," Am. Chem. Soc., Div. Pet. Chem, Miami Beach Meeting, Sep. 10-15, 1989, vol. 34, No. 3, pp. 583-588.

Schofer, Susan J., et al., "Studies of a Chromium-Based Ethylene Oligomerization System," INOR 817, Abstracts of Papers, 225th Am. Chem. Soc. National Meeting, New Orleans, LA, Mar. 23-27, 2003, 1 pg.

Small, Brooke L., et al., "Highly active iron and cobalt catalysts for the polymerization of ethylene," Journal of the American Chemical Society, 1998, pp. 4049-4050 plus cover page, vol. 120, No. 16, American Chemical Society.

Small, Brooke L., et al., "Iron-based catalysts with exceptionally high activities and selectivities for oligomerization of ethylene to linear a-olefins," Journal of the American Chemical Society, 1998, pp. 7143-7144 plus cover page, vol. 120, No. 28, American Chemical Society.

Small, Brooke L., et al., "Polymerization of propylene by a new generation of iron catalysts: mechanisms of chain initiation, propagation, and termination," Macromolecules, 1999, pp. 2120-2130, vol. 32, No. 7, American Chemical Society.

Sui, Junlong, et al., "Synthesis of 1-Hexene by trimerization of ethylene," China Synthetic Resin and Plastics, vol. 18, No. 2, 2001, pp. 23-25, 43.

Tamura, Takao, "Recent trends in a -olefin manufacturing technology," Idemitsu Giho, vol. 38, No. 3, 1995, pp. 266-269.

Tobisch, Sven, et al., "Catalytic Linear Oligomerization of Ethylene to Higher a-Olefins: Insight into the Origin of the Selective Generation of 1-Hexene Promoted by a Cationic Cyclopentadienyl-Arene Titanium Active Catalyst," Organometallics, vol. 22, No. 26, 2003, pp. 5392-5405.

Tobisch, Sven, et al., "Catalytic Oligomerization of Ethylene to Higher Linear a-Olefins Promoted by Cationic Group 4 Cyclopentadienyl•Arene Active Catalysts: A DFT Investigation Exploring the Influence of Electronic Factors on the Catalytic Properties by Modification of the Hemilabile Arene Functionality," Organometallics, vol. 23, No. 17, 2004, pp. 4077-4088.

Tobisch, Sven, et al., "Catalytic Oligomerization of Ethylene to Higher Linear a-Olefins Promoted by the Cationic Group 4 [(ns-Cp-(CMe2- bridge)-Ph)Mh (M=Ti, Zr, Hf) Active Catalysts: A Density Functional Investigation of the Influence of the Metal on the Catalytic Activity and Selectivity," JACS Articles, J. Am. Chem: Soc., vol. 126, No. 29, 2004, pp. 9059-9071.

Tobisch, Sven, et al., "Catalytic Oligomerization of Ethylene to Higher Linear cc-Olefins Promoted by Cationic Group 4 Cyclopentadienyl•Arene Active Catalysts: Toward the Computational Design of Zirconium- and Hafnium-Based Ethylene Trimerization Catalysts," Organometallics, vol. 24, No. 2, 2005, pp. 256-265.

Van Rensburg, Werner Janse, et al., "A DFT Study toward the Mechanism of Chromium-Catalyzed Ethylene Trimerization," Organometallics, vol. 23, No. 6, 2004, pp. 1207-1222.

Wu, Tianzhi, et al., "Catalytic trimerization of ethylene by half-sandwich titanium complexes bearing a pendant ethereal group," Journal of Molecular Catalysis A: Chemical, vol. 214, 2004, pp. 227-229.

Yang, Y., et al., "Roles of chloro compound in homogeneous [Cr(2-ethylhexanoate)3/2,5-dimethylpyrrole/triethylaluminum/chloro compound] catalyst system for ethylene trimerization," Applied Catalysis A: General, vol. 193, 2000, pp. 29-38.

Ye, Zhibin, et al., "A Tandem Catalytic System for the Synthesis of Ethylene-Hex-1-ene Copolymers from Ethylene Stock," Macromol. Rapid Commun., vol. 25, 2004, pp. 647-652.

Yu, Zhi-Xiang, "Theoretical Studies of the Mechanisms of Ethene Trimerization by TA- and CR-Based Catalysts," INOR 857, Abstracts of Papers, 225th Am. Chem. Soc. National Meeting, New Orleans, LA, Mar. 23-27, 2003, I pg.

Yu, Zhi-Xiang, et al., "Why Trimerization? Computational Elucidation of the Origin of Selective Trimerization of Ethene Catalyzed by [TaC13(C}13)2] and An Agostic-Assisted Hydride Transfer Mechanism," Angew. Chem. Int. Ed., vol. 42, No. 7, 2003, pp. 808-811.

Esteruelas, Miguel A., et al., "Preparation, Structure and Ethylene Polymerization Behavior of Bis (imino) pyridyl Chromium(III) Complexes," Organometallics—American Chemical Society, Jan. 1, 2003, pp. 395-406, vol. 22.

Small, Brooke L., et al., "Iron Catalysts for the Head-to-Head Dimerization of a-Olefins and Mechanistic Implications for the Production of Linear a-Olefins," Organometallics—American Chemical Society, Nov. 22, 2001, pp. 5738-5744, vol. 20.

Notice of Allowance dated Jun. 15, 2010, (11 pages), U.S. Appl. No. 11/928,756, filed Oct. 30, 2007.

Office Action dated Jun. 9, 2010, (72 pages), U.S. Appl. No. 11/963,252, filed Dec. 21, 2007.

Foreign communication from a counterpart application, EP05723401.5, Examination Report, May 4, 2010, 7 pages.

Advisory Action dated Aug. 9, 2006 (3 pages), U.S. Appl. No. 10/783,429, filed Feb. 20, 2004.

Advisory Action dated Mar. 29, 2007 (3 pages), U.S. Appl. No. 10/783,429, filed Feb. 20, 2004.

Office Action dated May 24, 2005 (6 pages), U.S. Appl. No. 10/783,429, filed Feb. 20, 2004.

Office Action dated Aug. 31, 2005 (13 pages), U.S. Appl. No. 10/783,429, filed Feb. 20, 2004.

Office Action dated Jan. 18, 2006 (15 pages), U.S. Appl. No. 10/783,429, filed Feb. 20, 2004.

Office Action dated May 24, 2006 (8 pages), U.S. Appl. No. 10/783,429, filed Feb. 20, 2004.

Office Action dated Sep. 7, 2006 (4 pages), U.S. Appl. No. 10/783,429, filed Feb. 20, 2004.

Office Action (Final) dated Jan. 9, 2007 (13 pages), U.S. Appl. No. 10/783,429, filed Feb. 20, 2004.

Office Action dated Apr. 19, 2007 (8 pages), U.S. Appl. No. 10/783,429, filed Feb. 20, 2004.

Office Action dated Sep. 28, 2007 (8 pages), U.S. Appl. No. 10/783,429, filed Feb. 20, 2004.

Advisory Action dated May 21, 2009 (3 pages), U.S. Appl. No. 11/207,232, filed Aug. 19, 2005.

Office Action dated Jun. 26, 2008 (16 pages), U.S. Appl. No. 11/207,232, filed Aug. 19, 2005.

Office Action (Final) dated Feb. 3, 2009 (15 pages), U.S. Appl. No. 11/207,232, filed Aug. 19, 2005.

Office Action dated Nov. 28, 2008 (43 pages), U.S. Appl. No. 12/057,853, filed Mar. 28, 2008.

Office Action dated Aug. 8, 2007 (13 pages), U.S. Appl. No. 10/782,554, filed Feb. 19, 2004.

Office Action dated Feb. 7, 2008 (6 pages), U.S. Appl. No. 10/782,554, filed Feb. 19, 2004.

Office Action dated Dec. 8, 2008 (41 pages), U.S. Appl. No. 10/782,554, filed Feb. 19, 2004.

Office Action (Final) dated Aug. 3, 2009 (20 pages), U.S. Appl. No. 12/057,853, filed Mar. 28, 2008.

Office Action dated Jun. 12, 2009, (53 pages) U.S. Appl. No. 11/928,756, filed Oct. 30, 2007.

Office Action (Final) dated Feb. 4, 2010, (15 pages), U.S. Appl. No. 11/928,756, filed Oct. 30, 2007.

Foreign communication from a counterpart application, EP 05723396.7, Examination Report, Mar. 8, 2010, 3 pages.

Foreign communication from a counterpart application, AU 2006283779—Examination Report, Jun. 11, 2010, 2 pages.

Foreign communication from a counterpart application, PCT/US2008/083026, International Preliminary Report on Patentability, Jun. 22, 2010, 7 pages.

Office Action (Final) dated Apr. 28, 2010, (10 pages), U.S. Appl. No. 11/928,756, filed Oct. 30, 2007.

Office Action dated Jun. 21, 2010 (34 pages), U.S. Appl. No. 12/534,536, filed Aug. 3, 2009.

Foreign communication from a counterpart application CA2664894, Examination Report, Apr. 30, 2010, 4 pages.

* cited by examiner

OLEFIN OLIGOMERIZATION

CROSS-REFERENCE TO RELATED APPLICATIONS

This application is a divisional of patent application Ser. No. 10/782,554, filed Feb. 19, 2004, entitled "Olefin Oligomerization," also known as U.S. Patent Application Publication 2005/0187418A1 now abandoned; and the content of this application is related to the content of patent application Ser. No. 10/379,828, filed Mar. 4, 2003, entitled "Composition and Method for a Hexadentate Ligand and Bimetallic Complex for Polymerization of Olefins," also known as U.S. Pat. No. 7,045,632, each of which is incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention generally relates to ethylene oligomerization to alpha olefins.

BACKGROUND OF THE INVENTION

Olefins, also commonly known as alkenes, are important items of commerce. Their many applications include employment as intermediates in the manufacture of detergents, as more environmentally friendly replacements where refined oils might otherwise be used, as monomers, and as intermediates for many other types of products. An important subset of olefins are olefin oligomers, and one method of making olefin oligomers is via oligomerization of ethylene, which is a catalytic reaction involving various types of catalysts.

Examples of catalysts used commercially in polymerization and oligomerization of olefins include alkylaluminum compounds, certain nickel-phosphine complexes, and a titanium halide with a Lewis acid, such as diethylaluminum chloride. Some examples of catalysts, and in particular transition metal catalysts, employed in ethylene polymerization and oligomerization may be found in U.S. Pat. Nos. 5,955,555, 6,103,946, 6,683,187, WO 03/011876, WO 02/28805, and WO 01/58874, which are incorporated herein by reference.

Selective 1-hexene (S1H) catalysts are another example of catalysts employed in the production of olefins. S1H catalysts are designed to be selective for production of 1-hexene. Examples of such S1H catalysts may be found in U.S. Pat. Nos. 6,455,648, 6,380,451, 5,986,153, 5,919,996, 5,859,303, 5,856257, 5,814,575, 5,786,431, 5,763,723, 5,689,028, 5,563,312, 5,543,375, 5,523,507, 5,470,926, 5,451,645, and 5,438,027, which are incorporated herein by reference.

Applications and demand for olefin polymers and oligomers continue to multiply, and competition to supply them correspondingly intensifies. Thus, additional novel and improved catalysts, and methods of olefin polymerization and oligomerization, are desirable.

SUMMARY OF THE INVENTION

Provided is a method of oligomerizing alpha olefins. In an embodiment, an oligomerization catalyst system is contacted in at least one continuous reactor with a feed comprising olefins; an effluent comprising product olefins having at least four carbon atoms is withdrawn from the reactor; the oligomerization catalyst system comprises iron or cobalt, or combinations thereof; and the single pass conversion of ethylene is at least about 40 weight percent among product olefins having at least four carbon atoms. In another embodiment, the single pass conversion of ethylene comprises at least about 65 weight percent among product olefins having at least four carbon atoms. In another embodiment, product olefins of the effluent having twelve carbon atoms comprise at least about 95 weight percent 1-dodecene. In another embodiment, product olefins comprise at least about 80 weight percent linear 1-alkenes. In another embodiment, product olefins comprise at least about 20 weight percent alpha olefins having from about 8 to about 20 carbon atoms. In another embodiment, the oligomerization catalyst system provided comprises a selective 1-hexene (S1H) catalyst.

In an embodiment, the oligomerization catalyst system provided comprises a metal complex activated by a co-catalyst wherein the metal complex comprises a ligand having chemical structure I:

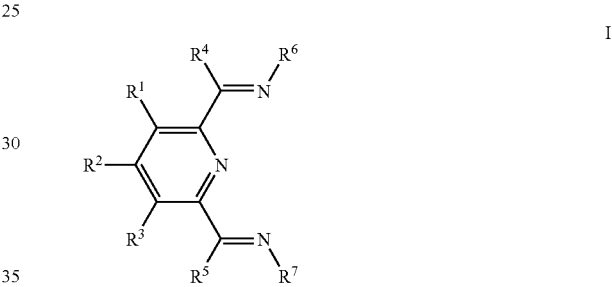

The components of the ligand having chemical structure I, labeled $R^1$ through $R^7$, may be defined as follows:

$R^1$, $R^2$, and $R^3$ are each independently hydrogen, hydrocarbyl, substituted hydrocarbyl, an inert functional group, or any two of $R^1$-$R^3$, vicinal to one another, taken together may form a ring;

$R^4$ and $R^5$ are each independently hydrogen, hydrocarbyl, substituted hydrocarbyl, or inert functional group;

$R^6$ and $R^7$ are each independently aryl, substituted aryl, optionally substituted heterohydrocarbyl moiety, optionally substituted aryl group in combination with and Π-coordinated to a metal, optionally substituted aromatic hydrocarbon ring, or optionally substituted polyaromatic hydrocarbon moiety.

Also provided is an oligomerization method comprising an oligomerization catalyst system contacted with a feed comprising olefins in at least one continuous reactor; a reactor effluent comprising product olefins having at least four carbon atoms; a single pass conversion of ethylene of at least about 65 weight percent among product olefins having at least four carbon atoms; and at least about 95 weight percent 1-dodecene among product olefins having twelve carbon atoms. In an embodiment, the oligomerization catalyst system comprises a metal alkyl or metal hydride species. In another embodiment, the at least one continuous reactor comprises a temperature of from about 40 to about 150 degrees Celsius. In another embodiment, the at least one continuous reactor comprises a loop reactor where fluid flow comprises a Reynolds number of from about 200,000 to about 700,000. In another embodiment, the at least one continuous reactor comprises a tubular reactor where fluid flow comprises a Reynolds number of from about 300,000 to about 2,000,000.

DETAILED DESCRIPTION OF THE INVENTION

Figure 1:
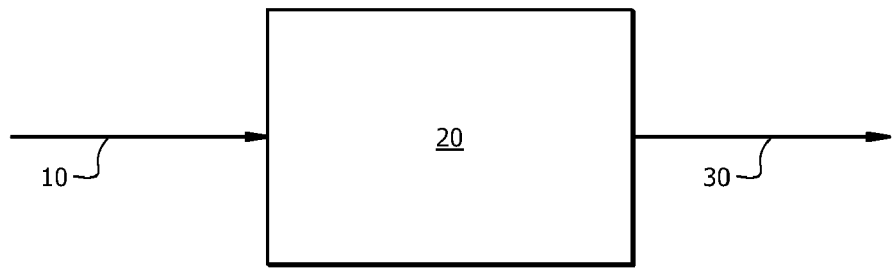
FIG. 1 illustrates an embodiment of an oligomerization reactor in accordance with the method provided.

FIG. 1 illustrates an embodiment of a method for oligomerization of alpha olefins. A feed 10 comprising olefins may be contacted with an oligomerization catalyst system. In an embodiment, the oligomerization catalyst system comprises iron or cobalt. In another embodiment, the feed 10 comprises ethylene. Oligomerization of the feed 10 may take place in a continuous reactor 20, and an oligomerization reactor effluent 30 including at least three components is withdrawn from the reactor 20. The components of the oligomerization effluent 30 may comprise diluent, product olefins, any ethylene not consumed by oligomerization, and catalyst system constituents. Product olefins of the effluent 30 comprise olefins having at least four carbon atoms that are produced by the oligomerization reaction in the reactor 20. In an embodiment, product olefins of the effluent 30 comprise alpha olefins having at least four carbon atoms that are produced by the oligomerization reaction in the reactor 20. The diluent comprises the remaining components of the effluent 30, other than product olefins, ethylene, and catalyst system constituents.

In an embodiment, oligomerization to product olefins having at least four carbon atoms comprises a single pass conversion of ethylene of at least about 40 weight percent. The single pass conversion may be expressed as the weight percent of reactant in the feed, e.g., ethylene, that is oligomerized during a single pass through the reactor. By calculation, the single pass conversion of ethylene may be the ratio, expressed as a percentage, of the mass of product olefins in the effluent divided by the mass of ethylene in the feed. The single pass conversion may also be expressed as the probability, expressed as a percentage, that one molecule of reactant in the feed, e.g., ethylene, will be oligomerized in the course of a single pass through the reactor. In another embodiment, oligomerization of ethylene to product olefins having at least four carbon atoms comprises a single pass conversion of ethylene of at least about 50 weight percent. In another embodiment, the oligomerization comprises a single pass conversion of ethylene of at least about 65 weight percent. In another embodiment, the oligomerization comprises a single pass conversion of ethylene of at least about 75 weight percent. In another embodiment, the oligomerization comprises a single pass conversion of ethylene of at least about 85 weight percent.

In addition to ethylene conversion, product quality and purity characterize the oligomerization described herein. In an embodiment, the effluent from the oligomerization reactor includes product olefins having at least four carbon atoms that comprise at least about 80 weight percent linear 1-alkenes. In another embodiment, the effluent from the oligomerization reactor includes from about 25 to about 95 weight percent product olefins having at least four carbon atoms. In another embodiment, the effluent includes at least about 40 weight percent product olefins having at least four carbon atoms. In another embodiment, the effluent includes from about 30 to about 80 weight percent product olefins having at least four carbon atoms. In another embodiment, the effluent includes from about 40 to about 70 weight percent product olefins having at least four carbon atoms. In another embodiment, the effluent includes from about 45 to about 65 weight percent product olefins having at least four carbon atoms. In another embodiment, the effluent includes from about 50 to about 60 weight percent product olefins having at least four carbon atoms. In another embodiment, the effluent comprises from about 50 to about 90 weight percent product olefins having at least four carbon atoms. In another embodiment, the effluent comprises from about 60 to about 90 weight percent product olefins having at least four carbon atoms. In another embodiment, the effluent comprises from about 70 to about 85 weight percent product olefins having at least four carbon atoms.

In an embodiment of the oligomerization, product olefins having at least four carbon atoms comprise olefins having from about 8 to about 20 carbon atoms. In another embodiment, product olefins having at least four carbon atoms comprise at least about 20 weight percent olefins having from about 8 to about 20 carbon atoms. In another embodiment, product olefins having at least four carbon atoms comprise at least about 30 weight percent olefins having from about 8 to about 20 carbon atoms. In another embodiment, product olefins having at least four carbon atoms comprise at least about 40 weight percent olefins having from about 8 to about 20 carbon atoms. In another embodiment, product olefins having at least four carbon atoms comprise at least about 20 weight percent olefins having from about 6 to about 20 carbon atoms. In another embodiment, product olefins having at least four carbon atoms comprise at least about 35 weight percent olefins having from about 6 to about 20 carbon atoms. In another embodiment, product olefins having at least four carbon atoms comprise at least about 50 weight percent olefins having from about 6 to about 20 carbon atoms. In another embodiment, product olefins having at least four carbon atoms comprise at least about 60 weight percent olefins having from about 6 to about 20 carbon atoms.

Selectivity for hexene may be of interest among the product olefins. In an embodiment, product olefins comprise at least about 20 weight percent olefins having 6 carbon atoms. In another embodiment, product olefins comprise from about 25 to about 70 weight percent olefins having 6 carbon atoms. In another embodiment, product olefins comprise from about 30 to about 60 weight percent olefins having 6 carbon atoms. In another embodiment, product olefins comprise from about 40 to about 50 weight percent olefins having 6 carbon atoms. In another embodiment, of the product olefins having 6 carbon atoms, at least about 98 weight percent are 1-hexene.

The purity of octenes and dodecenes among product olefins may also be of interest. In an embodiment, product olefins having 8 carbon atoms comprise at least about 95 weight percent 1-octene. In another embodiment, product olefins having 8 carbon atoms comprise at least about 96 weight percent 1-octene. In another embodiment, product olefins having 8 carbon atoms comprise at least about 97 weight percent 1-octene. In another embodiment, product olefins having 8 carbon atoms comprise at least about 98 weight percent 1-octene. In another embodiment, product olefins having 8 carbon atoms comprise at least about 99 weight percent 1-octene. In another embodiment, product olefins having 12 carbon atoms comprise at least about 93 weight percent 1-dodecene. In another embodiment, product olefins having 12 carbon atoms comprise at least about 95 weight percent 1-dodecene. In another embodiment, product olefins having 12 carbon atoms comprise at least about 96 weight percent 1-dodecene. In another embodiment, product olefins having 12 carbon atoms comprise at least about 97 weight percent 1-dodecene. In another embodiment, product olefins having 12 carbon atoms comprise at least about 98 weight percent 1-dodecene.

An oligomerization catalyst system is employed in the oligomerization provided. The oligomerization catalyst system may be homogeneous, heterogeneous, supported, or unsupported, as those terms are known in the art. In an embodiment, the oligomerization catalyst system comprises a co-catalyst, and a ligand complexed with a metal. In another embodiment, the oligomerization catalyst system comprises a metal complex activated by a co-catalyst, wherein the metal complex comprises a ligand having chemical structure I:

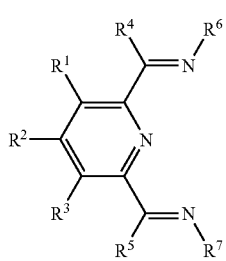

The components of the ligand having chemical structure I, labeled $R^1$ through $R^7$, may be defined as follows:

$R^1$, $R^2$, and $R^3$ are each independently hydrogen, hydrocarbyl, substituted hydrocarbyl, an inert functional group, or any two of $R^1$-$R^3$, vicinal to one another, taken together may form a ring;

$R^4$ and $R^5$ are each independently hydrogen, hydrocarbyl, substituted hydrocarbyl, or inert functional group;

$R^6$ and $R^7$ are each independently aryl, substituted aryl, optionally substituted heterohydrocarbyl moiety, optionally substituted aryl group in combination with and Π-coordinated to a metal, optionally substituted aromatic hydrocarbon ring, or optionally substituted polyaromatic hydrocarbon moiety.

The metal complex provided may be formed by complexing a ligand, such as, for example, the ligand having chemical structure I, with a metal. In an embodiment, the metal selected for complexing with a ligand to form the metal complex provided comprises a transition metal. In other embodiments, the metal selected to form the metal complex comprises iron, nickel, palladium, cobalt, vanadium, chromium, or combinations thereof. In another embodiment, the metal comprises iron, cobalt, or combinations thereof. In another embodiment, the oligomerization catalyst system comprises chromium.

Other variations on the oligomerization catalyst system are presented. For example, the order of addition of reagents may vary. In an embodiment, activating the metal complex, occurs in the absence of ethylene.

Referring to chemical structure I, the configuration of the ligand may vary with selection of $R^1$ through $R^7$. In an embodiment, $R^1$-$R^7$ are selected such that the ligand having chemical structure I is symmetrical. A symmetrical ligand as provided herein is symmetrical if it possesses symmetry higher than '$C_1$' symmetry, where $C_1$ refers to the $C_1$ point group. In an embodiment, $R^1$-$R^7$ are selected such that the ligand having chemical structure I is asymmetrical. An asymmetrical ligand as provided herein is asymmetrical if it possesses only '$C_1$' symmetry, i.e., possesses no mirror plane, no rotational axis of symmetry, and no inversion center.

The oligomerization catalyst system further comprises a co-catalyst, which may be involved in catalyst activation. In an embodiment, the co-catalyst comprises a metal alkyl or metal hydride species. In another embodiment, the co-catalyst comprises one or more Lewis acids; a combination of one or more Lewis acids and one or more alkylating agents; one or more alkyl aluminum compounds; one or more alkyl aluminoxanes; methyl aluminoxane (MAO); modified MAO; trialkyl aluminum; diethylaluminum chloride (DEAC); or combinations thereof. In another embodiment, the co-catalyst comprises triethylaluminum (TEA), trimethylaluminum (TMA), tri-isobutyl aluminum (TIBA), tri-butyl aluminum, or combinations thereof. In an embodiment, where the catalyst system comprises an iron catalyst, the molar ratio of aluminum to iron in the oligomerization ranges from about 1:1 to about 10,000:1. In another embodiment, where the catalyst system comprises an iron catalyst, the molar ratio of aluminum to iron in the oligomerization ranges from about 100:1 to about 3,000:1. In another embodiment, where the catalyst system comprises an iron catalyst, the molar ratio of aluminum to iron in the oligomerization ranges from about 200:1 to about 2,000:1.

Components of the oligomerization catalyst system may vary. In an embodiment, the oligomerization catalyst system comprises a metal complex activated by a co-catalyst, wherein the metal complex comprises a ligand having chemical structure II:

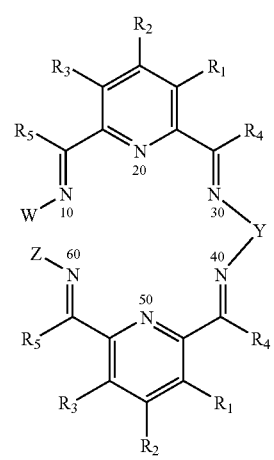

The components of the ligand having chemical structure II, labeled $R_1$-$R_5$, W, Y, and Z, may be defined as follows:

$R_1$, $R_2$, and $R_3$ are each independently hydrogen, hydrocarbyl, substituted hydrocarbyl, or an inert functional group;

$R_4$ and $R_5$ are each independently hydrogen, hydrocarbyl, an inert functional group, or substituted hydrocarbyl;

Y is a structural bridge, and W, Y, and Z independently comprise hydrogen, hydrocarbyl, an inert functional group, or substituted hydrocarbyl having from about 0 to about 30 carbon atoms.

In another embodiment of the oligomerization catalyst system, a metal complex is activated by a co-catalyst, wherein the metal complex may include a ligand having chemical structure III:

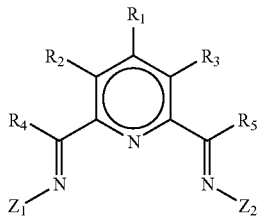

III

The components of the ligand having chemical structure III, labeled $R_1$-$R_5$, $Z_1$, and $Z_2$, may be defined as follows:

$R_1$-$R_5$ each comprise, independently, hydrogen, optionally substituted hydrocarbyl, an inert functional group, or any two of $R_1$-$R_3$ vicinal to one another taken together may form a ring;

$Z_1$, which is different from $Z_2$, is an aryl or substituted aryl group; and $Z_2$ comprises an aryl, substituted aryl, optionally substituted heterohydrocarbyl moiety, or an optionally substituted aryl group in combination with and Π-coordinated to a metal.

In another embodiment of the ligand having chemical structure III, $Z_2$ may be defined as an aryl, substituted aryl, optionally substituted aromatic heterocyclic moiety, an optionally substituted polyaromatic heterocyclic moiety, an optionally substituted aliphatic heterocyclic moiety, or an optionally substituted aliphatic heterohydrocarbyl moiety.

In another embodiment of the oligomerization catalyst system, a metal complex is activated by a co-catalyst, wherein the metal complex may include a ligand having chemical structure IV:

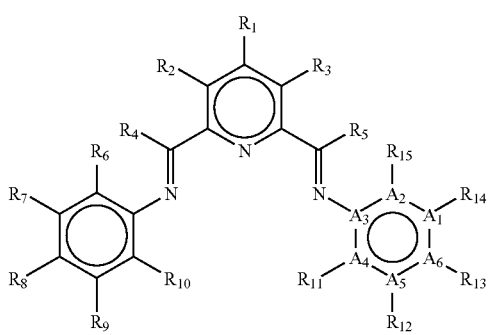

IV

The components of the ligand having chemical structure IV, labeled $R_1$-$R_{15}$ and $A_1$-$A_6$, may be defined as follows:

$A_1$-$A_6$ each comprise, independently, carbon, nitrogen, oxygen, or sulphur;

in the absence of $A_6$, $A_1$ may be directly bonded to $A_5$;

$R_1$-$R_{12}$, $R_{14}$-$R_{15}$, and, if present, $R_{13}$, are each, independently, hydrogen, optionally substituted hydrocarbyl, or an inert functional group;

any two of $R_1$-$R_{15}$, vicinal to one another, taken together may form a ring; and conditionally, when $A_1$-$A_5$ and $A_6$, if present, are all carbon, said atoms constitute the cyclopentadienyl or aryl part of a Π-coordinated metal.

In another embodiment of the oligomerization catalyst system, a metal complex is activated by a co-catalyst, wherein the metal complex may include a ligand having chemical structure V:

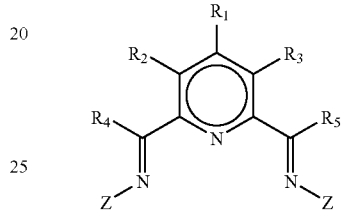

V

The components of the ligand having chemical structure V, labeled $R_1$-$R_5$ and Z, may be defined as follows:

$R_1$-$R_5$ are each, independently, hydrogen, substituted hydrocarbyl, an inert functional group, or any two of $R_1$-$R_3$, vicinal to one another, taken together may form a ring; and each Z, selected independent of the other, is a substituted aryl, an optionally substituted polyaromatic hydrocarbon moiety, an optionally substituted heterohydrocarbyl moiety, or a substituted aryl group in combination with a metal, said optionally substituted aromatic hydrocarbon ring being Π-coordinated to the metal.

In another embodiment of the oligomerization catalyst system, a metal complex is activated by a co-catalyst, wherein the metal complex may include a ligand having chemical structure VI:

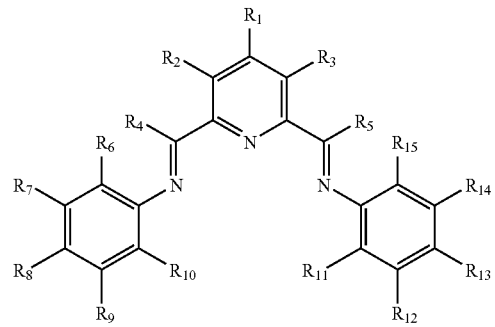

VI

The components of the ligand having chemical structure VI, labeled $R_1$-$R_{15}$, may be defined as follows:

$R_1$-$R_5$ and $R_7$-$R_9$ and $R_{12}$-$R_{14}$ are each, independently, hydrogen, substituted hydrocarbyl, an inert functional group, or any two of $R_1$-$R_3$, $R_7$-$R_9$, and $R_{12}$-$R_{14}$, vicinal to one another, taken together may form a ring; and $R_6$, $R_{10}$, $R_{11}$, and $R_{15}$ are identical and are selected from fluorine or chlorine.

In another embodiment of the oligomerization catalyst system, a metal complex is activated by a co-catalyst, wherein the metal complex may include a ligand having chemical structure VII:

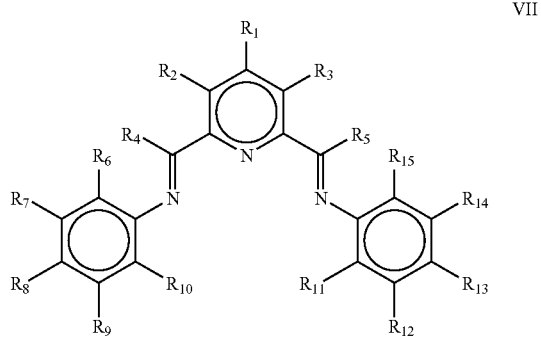

VII

The components of the ligand having chemical structure VII, labeled $R_1$-$R_{15}$, may be defined as follows:

$R_1$-$R_5$ and $R_7$-$R_9$ and $R_{12}$-$R_{14}$ are each, independently, hydrogen, substituted hydrocarbyl, an inert functional group, or any two of $R_1$-$R_3$, $R_7$-$R_9$, and $R_{12}$-$R_{14}$, vicinal to one another, taken together may form a ring;

$R_6$ is hydrogen, substituted hydrocarbyl, an inert functional group, or taken together with $R_7$ or $R_4$ to form a ring;

$R_{10}$ is hydrogen, substituted hydrocarbyl, an inert functional group, or taken together with $R_9$ or $R_4$ to form a ring; and $R_{11}$ and $R_{15}$ are each, independently, hydrogen or an inert functional group.

Figure 2:
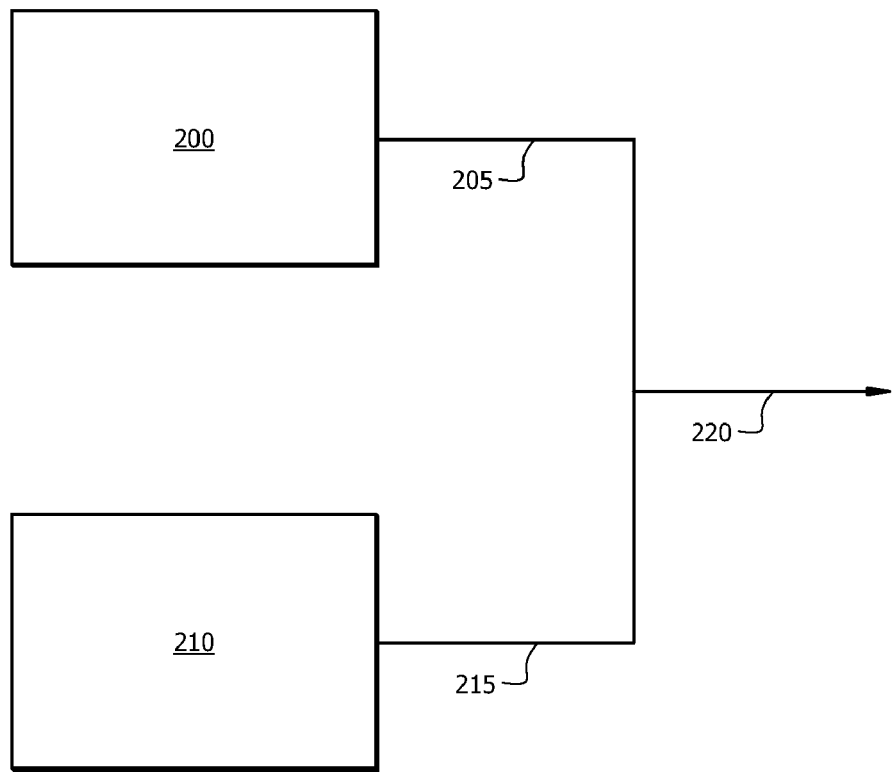
FIG. 2 illustrates an embodiment of a process design for simultaneous employment of combinations of catalysts in parallel reactors.
Figure 3:
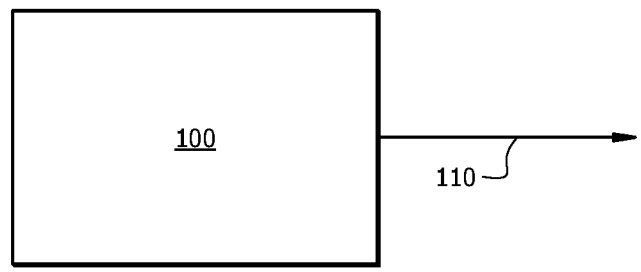
FIG. 3 illustrates an embodiment of a process design for simultaneous employment of combinations of catalysts in the same reactor.

The oligomerization catalyst system may include combinations of catalysts, which may modify the distribution of product olefins in the effluent. In an embodiment, the oligomerization catalyst system comprises a selective one hexene (S1H) catalyst. In another embodiment, the oligomerization catalyst system comprises a S1H catalyst; a metal complex including a ligand having chemical structure I, II, III, IV, V, VI, or VII, or combinations thereof, as provided herein; and at least one co-catalyst. In an embodiment where a combination of catalysts makes up the oligomerization catalyst system, an S1H catalyst; a metal complex including a ligand having chemical structure I, II, III, IV, V, VI, or VII, or combinations thereof; and said co-catalyst may be employed simultaneously. FIG. 2 illustrates an embodiment of a process design where combinations of different catalysts and co-catalysts may be employed simultaneously. A transition metal catalyst oligomerization may be executed in a first reactor 200, and simultaneously a S1H catalyst oligomerization may be executed in a parallel reactor 210. Alternatively, two different transition metal catalysts may be employed simultaneously in the two parallel reactors 200, 210, or a combination of transition metal and S1H catalysts may be employed simultaneously in the two parallel reactors 200, 210. The effluents 205, 215 of the reactors 200, 210 may be combined into a single process output stream 220. FIG. 3 illustrates another embodiment of a process design for simultaneous employment of combinations of transition metal and S1H catalysts and co-catalysts. Combinations of different transition metal catalysts, or combinations of transition metal catalysts and S1H catalysts, may be employed in the same reactor 100. Thus, the effluent 110 would include product olefins generated by each of the oligomerization catalysts employed in the reactor 100.

Figure 4:
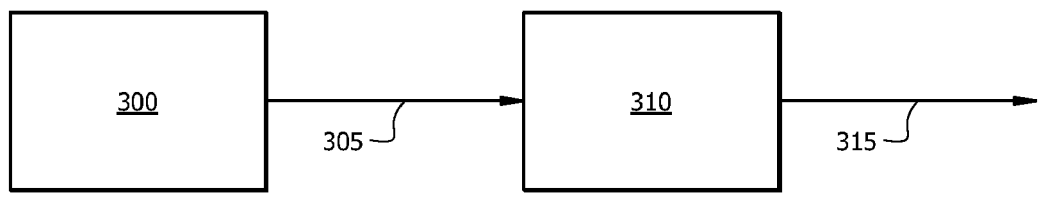
FIG. 4 illustrates an embodiment of a process design for consecutive employment of catalysts.

In another embodiment where a combination of catalysts makes up the oligomerization catalyst system, an S1H catalyst; a metal complex including a ligand having chemical structure I, II, III, IV, V, VI, or VII, or combinations thereof; and said co-catalyst may be employed consecutively. FIG. 4 illustrates an embodiment of a process design where catalysts may be employed consecutively. One type of oligomerization catalyst or combination of catalysts may be employed in a first reactor 300, and a second type of oligomerization catalyst or combination may be employed in a second reactor 310. The first 300 and second 310 reactors are operated in series. The first reactor effluent 305 is fed to the second reactor 310, so the second reactor effluent 315 comprises a mixture of the two reactor effluents 305, 315.

The particular combination of catalysts employed in a particular process design, such as, for example, those combinations and designs illustrated by FIGS. 2-4, may modify the distribution of product olefins in the effluent of an oligomerization process. Such a modification may cause the distribution of product olefins to vary from a typical Schulz-Flory distribution, and, therefore, also adjust the Schulz-Flory constant, or K-value associated with such a product olefin distribution. In an embodiment where an oligomerization catalyst system comprises a combination of catalysts, the product olefins of the oligomerization comprise a 1-hexene content of from about 20 to about 80 weight percent. In another embodiment, product olefins comprise a 1-hexene content of from about 50 to about 80 weight percent.

The lifetimes of the components of the oligomerization catalyst system may vary. For example, the lifetime of a catalyst including a metal complex may be different than the lifetime of an S1H-type catalyst. Thus, designing the oligomerization method as provided herein to account for such variances may be advantageous. In an embodiment, where the continuous reactor includes a tubular reactor, the oligomerization catalyst system is injected at more than one point along the length of the reactor. In another embodiment, a metal complex is injected at more than one point along the length of the reactor. In another embodiment, the oligomerization catalyst system and olefins are injected at more than one point along the length of the reactor.

The oligomerization provided may be a continuous process carried out in one or more reactors. In an embodiment, the reactor comprises a loop reactor, tubular reactor, continuous stirred tank reactor (CSTR), or combinations thereof.

The oligomerization may be further characterized by the velocity of reaction components in the continuous reactor, and associated Reynolds numbers. In an embodiment, the continuous reactor may be a loop reactor where fluid flow in the loop reactor comprises a Reynolds number of from about 100,000 to about 1,000,000. In another embodiment, the continuous reactor may be a loop reactor where fluid flow in the loop reactor comprises a Reynolds number of from about 200,000 to about 700,000. In another embodiment, the continuous reactor may be a tubular reactor where fluid flow in the tubular reactor comprises a Reynolds number of from about 100,000 to about 10,000,000. In another embodiment, the continuous reactor may be a tubular reactor where fluid flow in the tubular reactor comprises a Reynolds number of from about 300,000 to about 2,000,000.

In various embodiments, the continuous reactor may be employed in the form of different types of reactors in combination, and in various arrangements. In an embodiment, the continuous reactor may be a combination of a tubular reactor and a CSTR. In other embodiments, the continuous reactor may be employed as reactors in series, reactors in parallel, or combinations thereof. In an embodiment, the continuous reactor may be more than one CSTR in series. In another embodiment, the continuous reactor may be a tubular reactor and a loop reactor in series.

It is known in the art that the temperatures associated with oligomerization may vary depending on the oligomerization catalyst system employed. For example, oligomerizations employing transition metal catalysts typically involve lower temperatures. Such lower reactor temperatures, however, may make precipitation of waxes and, therefore, plugging more problematic. Such waxes that cause plugging may be, for example, the insoluble portion of wax products from the oligomerization reaction that have at least 20 carbon atoms. The turbidity, or clarity of the reactor contents upon visual inspection may be an indicator of the presence of precipitated waxes. As the level of precipitated waxes in the reactor increases, the turbidity of the reactor contents also typically increases. Thus, lower reactor temperatures and potential increases in wax precipitation and plugging may be characteristic of oligomerization. In an embodiment, at least one oligomerization reactor comprises a temperature of from about 40 to about 150 degrees Celsius. In another embodiment, at least one reactor comprises a temperature of from about 40 to about 90 degrees Celsius. In another embodiment, at least one reactor comprises a temperature of from about 80 to about 150 degrees Celsius. In another embodiment, the contents of the reactor at steady state, even without substantial turbulence, are not turbid.

A diluent, or solvent is among the components of the oligomerization. At lower oligomerization temperatures, such as those associated with late transition metal catalysts, selection of diluent may contribute to prevention of wax precipitation and, therefore, affect the turbidity of reactor contents, and plugging. In embodiments, the diluent comprises aliphatics, non-aliphatics, aromatics, saturated compounds having from 4 to 8 carbon atoms, or combinations thereof. In other embodiments, the diluent comprises cyclohexane, heptane, benzene, toluene, xylene, ethylbenzene, or combinations thereof. In another embodiment, the diluent comprises an aromatic compound having from about 6 to about 30 carbon atoms. In another embodiment, the diluent comprises olefins. In another embodiment, the diluent comprises alpha olefins. In another embodiment, the diluent comprises olefins having from about 4 to about 30 carbon atoms. In another embodiment, the diluent comprises olefins having from about 4 to about 12 carbon atoms. In another embodiment, the diluent comprises olefins having from about 10 to about 30 carbon atoms. In another embodiment, the diluent comprises olefins having from about 12 to about 18 carbon atoms. In yet other embodiments, the diluent comprises 1-butene, 1-dodecene, 1-tetradecene, 1-hexadecene, 1-octadecene, or combinations thereof. In another embodiment, the diluent comprises 1-tetradecene. In another embodiment, the diluent comprises no more than about 30 weight percent of the oligomerization reactor effluent. In another embodiment, the diluent comprises no more than about 20 weight percent of the reactor effluent. In another embodiment, the diluent comprises no more than about 10 weight percent of the reactor effluent.

As is known in the art, coolants may be employed when operating oligomerization reactors. For example, vaporized water may be used to cool an oligomerization reactor. Accordingly, as oligomerization temperature may vary with the type of catalyst employed, so may the coolant employed to cool the reactor. In an embodiment, a coolant more volatile than water is used in cooling the continuous reactor. In another embodiment, the coolant employed comprises butane, isobutane, isopentane, or combinations thereof.

Reactor, or ethylene pressure may impact the product olefins of the oligomerization. In an embodiment, the distribution of product olefins in the effluent is manipulated via modifying reactor pressure. In an embodiment, where reactor pressure is modified in order to manipulate product olefin distribution, the oligomerization catalyst system includes a transition metal complex and a co-catalyst, and the co-catalyst is a tri-alkyl aluminum.

Further provided is a method that comprises contacting a feed comprising olefins and an oligomerization catalyst system. The feed is oligomerized in at least one continuous reactor, and an effluent comprising product olefins that have at least four carbon atoms is withdrawn from the reactor. In an embodiment, the method of oligomerization to product olefins having at least four carbon atoms is further characterized by a single pass conversion of ethylene of at least about 65 weight percent. Additionally, the product olefins from the oligomerization that have twelve carbon atoms comprise at least about 95 weight percent 1-dodecene.

In embodiments of the method comprising a single pass conversion of ethylene of at least about 65 weight percent, and product olefins having twelve carbon atoms that comprise at least about 95 weight percent 1-dodecene, the oligomerization catalyst system may comprise a metal complex activated by a co-catalyst where the metal complex comprises a ligand having one or more of chemical structures I-VIII, or combinations thereof. In another embodiment, the oligomerization catalyst system may comprise an S1H catalyst. In other embodiments, the oligomerization catalyst system may comprise iron, cobalt, chromium, nickel, vanadium, or combinations thereof.

The present application further discloses a method of oligomerizing alpha olefins where a metal complex having chemical structure VIII is contacted with a co-catalyst and a feed comprising olefins.

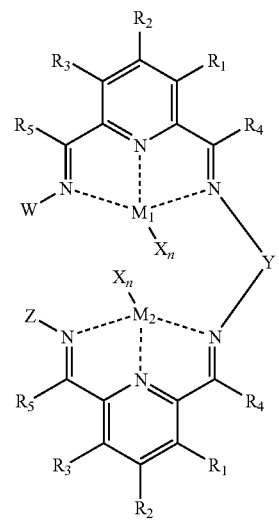

VIII

The metal complex having chemical structure VIII may be produced from a ligand having chemical structure II as provided herein. The metal complex VIII may be formed as a result of a coordination reaction between the ligand II and a metal salt. In an embodiment, the components of the metal complex of chemical structure VIII, labeled as $R_1$-$R_5$, W, Y, Z, M, and $X_n$ are as follows:

wherein $R_1$, $R_2$, and $R_3$ are each independently hydrogen, hydrocarbyl, substituted hydrocarbyl, or an inert functional group;

$R_4$ and $R_5$ are each independently hydrogen, hydrocarbyl, an inert functional group, or substituted hydrocarbyl; and Y is a structural bridge, and W, Y, and Z are independently hydrogen, hydrocarbyl, an inert functional group, or substituted hydrocarbyl having from about 0 to about 30 carbon atoms.

wherein $M_1$ and $M_2$ are metal atoms that are independently selected from a group comprising cobalt, iron, chromium, and vanadium;

each X is an anion; and n is 1, 2, or 3, so that the total number of negative charges on X is equal to the oxidation state of $M_1$ or $M_2$.

EXAMPLES

The following examples, 1 through 3, are merely representative of aspects of the present invention and, as one skilled in the art would recognize, the present invention may be practiced without many of the aspects illustrated by the examples. Data in examples 2 and 3 that represent process components, and compositions of reaction mixtures and products were determined by gas chromatography using a standard boiling point capillary column and flame ionization detector (GC/FID).

Example 1

Several α-olefin mixtures were mixed separately with two diluents, cyclohexane and 1-tetradecene. The level of diluent in each mixture was varied between 10 and 27 percent to simulate a reactor effluent, excluding unreacted ethylene, with from 90 to 73 percent product composition, respectively. The amounts of wax in the mixtures were gradually increased such that the total amount of wax in the mixtures ranged from 10 to 15 percent. The temperatures of the mixtures were then varied from 35 to 65° C. for each mixture, in order to determine when each mixture would become a clear solution.

Using a typical commercial Schulz-Flory chain growth factor of K=0.7, where $K = (\text{moles } C_{n+2})/(\text{moles } C_n)$, 500 g of a mixture containing 135 g of diluent (either cyclohexane or 1-tetradecene) and 365 g of α-olefins were prepared in a 1 L flask fitted with a heating mantle. A stir bar was added to the flask, which was sealed and then connected to a bubbler via a needle in order to relieve pressure. Due to the volatility of 1-butene and 1-hexene, their masses were combined with the mass of 1-octene for preparing the solutions, such that 1-octene was used to simulate the presence of 1-butene, 1-hexene and 1-octene (see Table 1). Similarly, 1-dodecene was used to represent the $C_{10}$, $C_{12}$, and $C_{14}$ fractions, and 1-octadecene was used to represent the $C_{16}$ and $C_{18}$ fractions. For the waxes, $C_{20/24}$, $C_{26/28}$, and $C_{30}$ were chosen to represent the wax products made by the catalysts of interest. In addition to these two mixtures, a third mixture was prepared in which only 50 g of 1-tetradecene diluent was used in 506 g of the mixture.

The three prepared mixtures, shown in columns 1-3 in Table 1, were then heated slowly with rapid stirring to determine the point at which each solution became clear. For the solution containing 73 percent product olefins and 27 percent $C_{14}$ diluent, the solution became clear at 55° C. (col. 1), and when the diluent concentration was lowered to 10.3 percent (col. 3), the solution became clear at 60° C. Contrasting these results, the mixture containing cyclohexane (col. 2) did not become clear under any of the temperature conditions studied. The results would suggest that a mid-range α-olefin fraction, such as 1-tetradecene, may be a better solvent and less likely to promote reactor plugging than cyclohexane. Also, the high level of product in the effluent suggests that it may be possible to run an oligomerization of this sort at low temperatures and high conversions without causing lines to plug.

To test the limits of reactor composition, further experiments were performed in which the amount of wax in the reactor was artificially inflated. Columns 4, 5, and 6 in Table 1 illustrate the respective changes that were made to solutions 1, 2, and 3. In each mixture the amount of diluent and non-wax olefins was held constant, but the amount of $C_{20+}$ waxes was increased by about 30 percent. As expected, the cyclohexane mixture 5 was cloudy at all of the temperatures studied. However, the 26 percent diluent (col. 4) and the 10 percent diluent (col. 6) mixtures were completely clear at 40 and 45° C., respectively. For solutions 1 and 3, the "clear" point was determined by slowly raising the temperature, but for solutions 4 and 6, the point of total clarity was determined by slowly lowering an already elevated temperature.

As a final incremental change, solutions 7 and 8 were prepared, in which the amount of wax in solutions 4 and 6 was increased. In this case, all of the additional wax was $C_{30}$ or higher, so that the amount of higher molecular weight material could be exaggerated. With these elevated amounts of wax, the solutions were still clear at 40 and 45° C., respectively.

TABLE 1

| Component (all in grams) | Mixture | | | | | | | |
|---|---|---|---|---|---|---|---|---|
| | 1 | 2 | 3 | 4 | 5 | 6 | 7 | 8 |
| C8 | 166 | 166 | 227 | 166 | 166 | 227 | 166 | 227 |
| C12 | 109 | 109 | 135 | 109 | 109 | 135 | 109 | 135 |
| Cyclohexane | 0 | 135 | 0 | 0 | 135 | 0 | 0 | 0 |
| C14 | 135 | 0 | 50 | 135 | 0 | 50 | 135 | 50 |
| C18 | 39 | 39 | 42 | 39 | 39 | 42 | 39 | 42 |
| C20/24 | 30 | 30 | 32 | 40 | 40 | 43 | 40 | 43 |
| C26/28 | 9 | 9 | 9.2 | 12 | 12 | 12.7 | 12 | 12.7 |
| C30 | 11 | 11 | 11.2 | 14.6 | 14.6 | 15 | 22 | 22.4 |
| Total (g) | 499 | 499 | 506 | 516 | 516 | 525 | 523 | 532 |
| % Diluent | 27 | 27 | 10 | 26 | 26 | 10 | 26 | 9 |
| % Wax | 10 | 10 | 10.3 | 12.9 | 12.9 | 13.5 | 14.1 | 14.7 |
| T (° C.) | | | | | | | | |
| 35 | a | a | a | b | a | b | b | b |
| 40 | a | a | a | c | a | b | c | b |
| 45 | b | a | a | c | a | c | c | c |
| 50 | b | b | b | c | a | c | c | c |
| 55 | c | b | b | c | a | c | c | c |
| 60 | c | b | c | c | a | c | c | c |
| 65 | c | b | c | c | a | c | c | c | a = very cloudy
b = slightly cloudy
c = totally clear

Example 2

Figure 5:
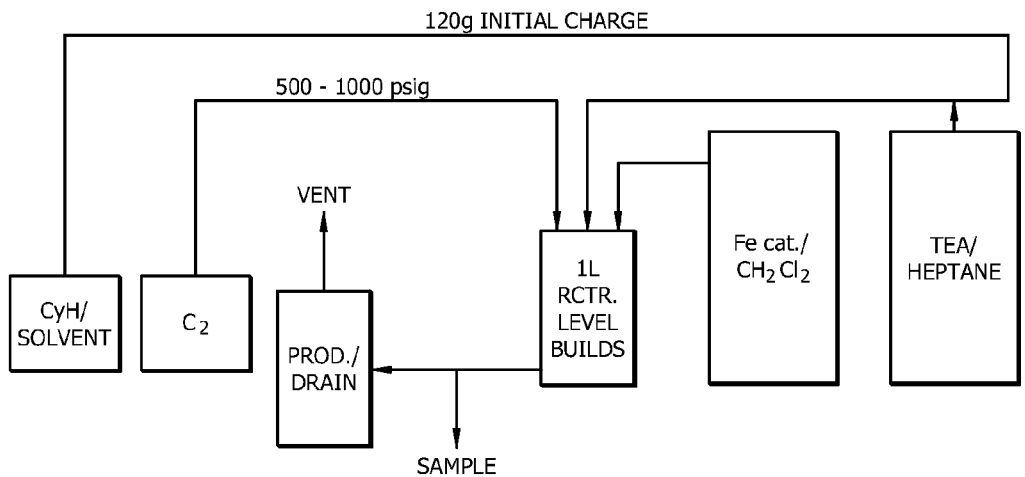
FIG. 5 illustrates an embodiment of a process design in accordance with the oligomerization provided.

Two specific iron catalysts were tested under semi-continuous operating conditions. FIG. 5 illustrates the process design for the test. 120 g of solvent was pumped into a 1.0 L reactor under inert conditions, and the reactor was then pressurized with ethylene to either 500 or 1000 psig. Next, high pressure pumps were used to quickly transfer the first hour's amounts of catalyst, which was the iron dichloride complex of either structure IX or X, and co-catalyst (TEA) to the reactor.

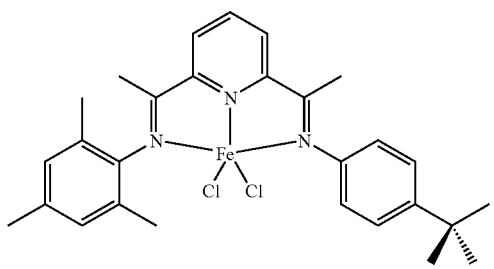

IX

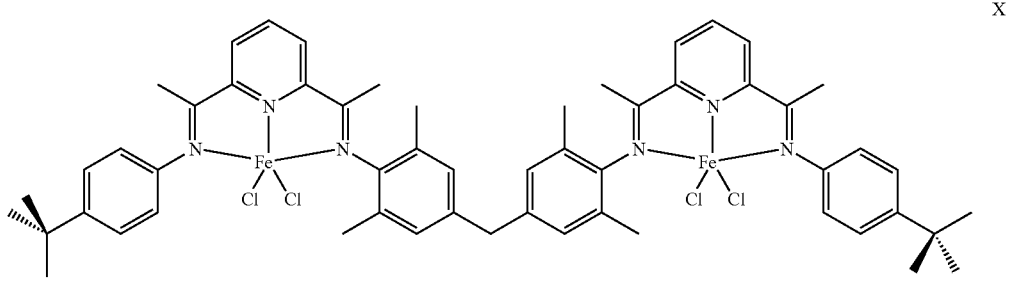

X

The catalyst was introduced as an anhydrous methylene chloride solution (0.1 mg/ml), and the co-catalyst was diluted in anhydrous heptane. The reaction was allowed to exotherm to the run temperature of 50° C., and this temperature was maintained by internal cooling coils in the reactor. The catalyst and co-catalyst pumps were allowed to continue running at the hourly rates shown in Table 2, and the ethylene was fed "on demand" using a pre-set regulator. The reaction was periodically sampled via the sampling port, and the data in Table 2 were generated via GC analysis. Entries 1-8 reflect data collected employing an iron catalyst formed from a ligand having chemical structure IX and $FeCl_2$, while Entry 9 reflects data collected under similar conditions but employing an iron catalyst formed from a ligand having chemical structure X and $FeCl_2$. The data shown for the product distributions and the product purities are from the last samples taken for each reaction, i.e. at the highest conversion level. Each reaction was run for approximately 3 hours after the reaction had exothermed to 50° C. The catalyst productivities in Table 2 are based on the total amount of product formed and the total amount of catalyst and co-catalyst fed to the reactor. The cyclohexane solvent was used as the internal standard for calculating the catalyst productivities.

TABLE 2

| | Entry | | | | | | | | |
|---|---|---|---|---|---|---|---|---|---|
| | 1 | 2 | 3 | 4 | 5 | 6 | 7 | 8 | 9 |
| Solvent (120 g) | $C_6H_{12}$ | $C_6H_{12}$ | $C_6H_{12}$ | $C_6H_{12}$ | $C_6H_{12}$ | $C_6H_{12}$ | $C_6H_{12}$ | 1-Butene | $C_6H_{12}$ |
| Catalyst | IX | IX | IX | IX | IX | IX | IX | IX | X |
| Flowrate (mg/hr) | 0.4 | 0.4 | 0.2 | 0.2 | 0.4 | 0.4 | 0.2 | 0.2 | 0.2 |
| Yield (g) of product AOs | 322 | 214 | 459 | 326 | 343 | 329 | 118 | 312 | 374 |
| lb prod/lb Al | 4464 | 2321 | 5200 | 6170 | 3193 | 2997 | 1518 | 4227 | 5004 |
| lb prod/lb Fe cat ($\times 10^3$) | 224 | 116 | 521 | 620 | 321 | 301 | 76 | 424 | 509 |
| TEA:Fe ratio | 1000 | 1000 | 2000 | 2000 | 2000 | 2000 | 1000 | 2000 | 2000 |
| K (C20/C18) | 0.68 | 0.77 | 0.67 | 0.74 | 0.68 | 0.78 | 0.76 | 0.69 | 0.68 |
| K (C16/C14) | 0.68 | 0.76 | 0.69 | 0.76 | 0.68 | 0.78 | 0.77 | 0.69 | 0.69 |
| K (C10/C8) | 0.68 | 0.76 | 0.67 | 0.76 | 0.68 | 0.78 | 0.77 | 0.69 | 0.69 |
| P ethylene (psig) | 500 | 1000 | 500 | 1000 | 500 | 1000 | 1000 | 500 | 500 |
| 1-C6 Purity | 99.35 | 99.16 | 99.34 | 99.26 | 99.29 | 98.88 | 98.97 | 98.87 | 99.34 |
| C6 % branched AO | 0.16 | 0.03 | 0.19 | 0.14 | 0.16 | 0.07 | 0.03 | 0.47 | 0.17 |
| C6 % Paraffin | 0.24 | 0.29 | 0.19 | 0.15 | 0.38 | 0.27 | 0.38 | 0.19 | 0.21 |
| 1-C8 Purity | 99.13 | 99.16 | 99.07 | 99.05 | 99.17 | 98.69 | 98.98 | 98.27 | 99.05 |
| C8 % branched AO | 0.30 | 0.25 | 0.32 | 0.24 | 0.29 | 0.66 | 0.27 | 0.83 | 0.29 |

Figure 6:
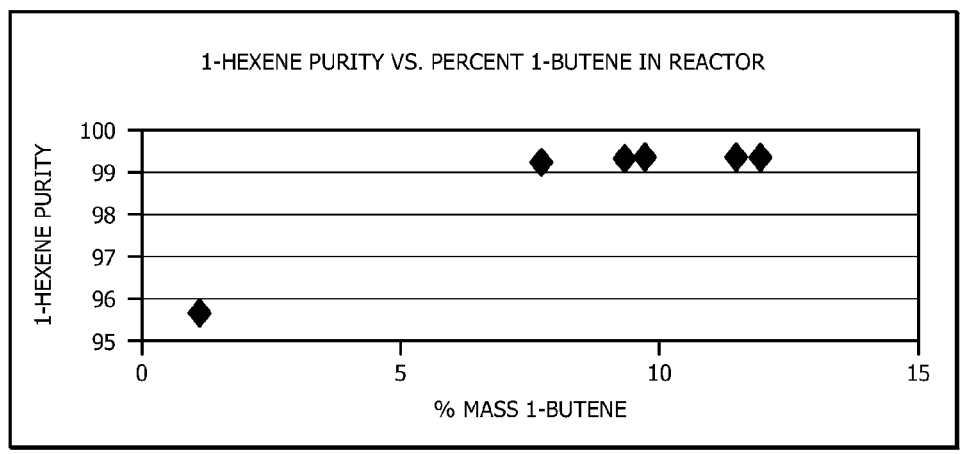
FIG. 6 illustrates 1-hexene quality for several embodiments of the oligomerization provided.
Figure 7:
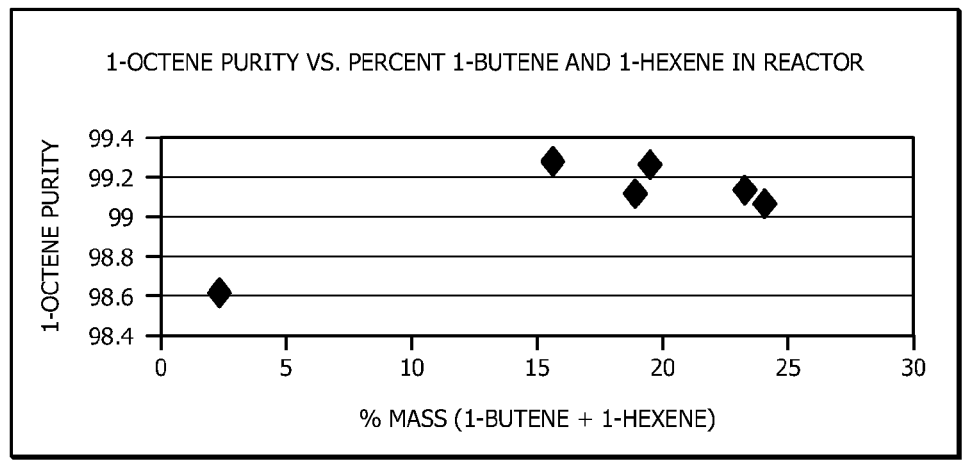
FIG. 7 illustrates 1-octene quality for several embodiments of the oligomerization provided.
Figure 8:
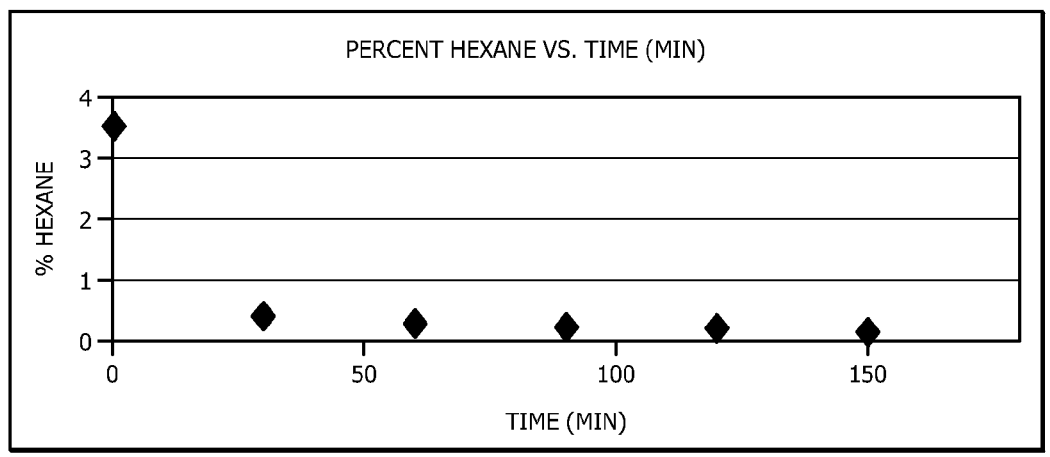
FIG. 8 illustrates changes in paraffin content over time while executing an embodiment of the oligomerization provided.

In examining Table 2, some additional observations are noted. First, the product distribution, as expressed by the Schulz-Flory K value, was approximately 0.67-0.69 at 500 psig ethylene pressure, and reflected pressure dependence. Upon increasing the pressure to 1000 psig, the K value increased to 0.75-0.77 (compare entries 1 and 2). Also, using the data in entry 3 of Table 2, FIGS. 6, 7, and 8 were created. FIG. 6 shows that when increasing the concentration of 1-butene in the reactor, the 1-hexene quality remains near 99.3 percent at 12 percent 1-butene concentration. FIG. 7 shows that the 1-octene purity remains over 99 percent with 25 percent 1-butene and 1-hexene in the reactor. FIG. 8 illustrates how the overall paraffin content in the reactor decreases with increasing conversion and run length.

Example 3

Figure 9:
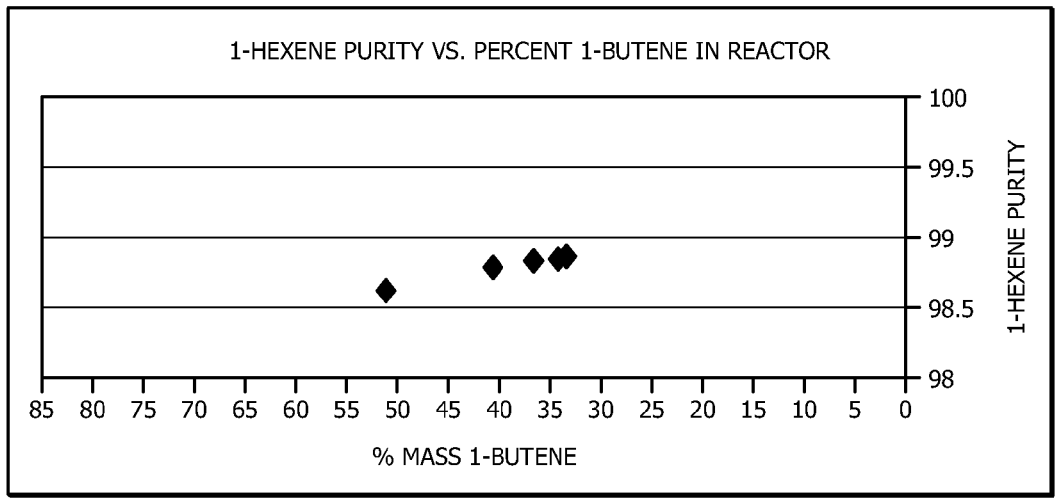
FIG. 9 illustrates 1-hexene purity for several embodiments of the oligomerization provided.
Figure 10:
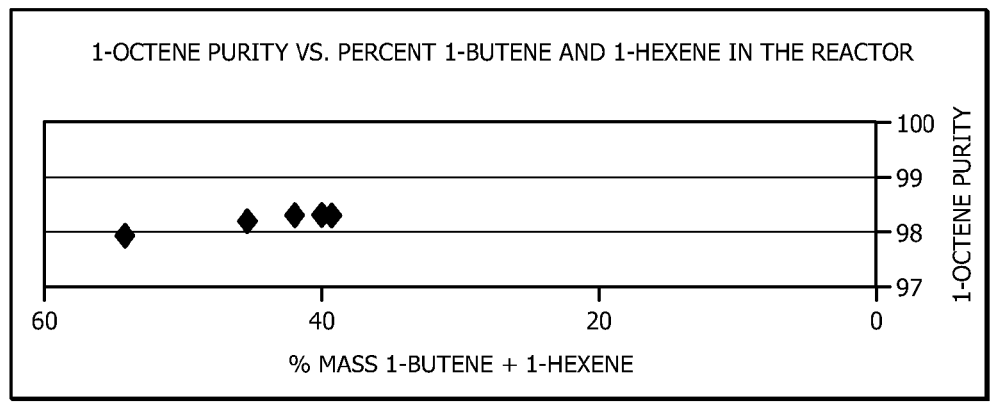
FIG. 10 illustrates 1-octene purity for several embodiments of the oligomerization provided.

The tests described in entry 8 of Example 2 are furthered described in Example 3. To examine the impact of ethylene conversion on product olefin quality, product olefin content was simulated utilizing 1-butene as a diluent, which is also one of the product olefins produced in the oligomerization reactor, rather than cyclohexane. See entries 3 and 8 of Table 2. Thus, 120 g of 1-butene was introduced into the reactor, followed by catalyst and cocatalyst. Ethylene was fed to the reactor by demand and the semi-continuous oligomerization experiment was performed at 500 psig of ethylene. In FIGS. 9 and 10, conversion, measured as the amount of product olefins formed, increases as the percentage of butene present decreases. In the single run oligomerization, the mass of the diluent, 1-butene, decreases from 100 percent due to ethylene oligomerization to product olefins. FIG. 9 indicates that a high 1-hexene purity was obtained in this run. The lowest 1-hexene purity point, near 50 mass percent 1-butene, is due to increased paraffin content (0.7 percent vs 0.2 percent for other points) resulting from low ethylene conversion. In FIG. 10, 1-Octene purity remains over 98 percent when running the reaction in 1-butene. As in FIG. 9, the elevated level of paraffin at low conversion artificially lowers the olefin purity. FIGS. 9 and 10, which were composed using data from the 500 psig run, may be viewed as extensions of FIGS. 6 and 7, respectively. When using 1-butene as the solvent, the product quality remains high, approaching 99 percent for 1-hexene and exceeding 98.2 percent for 1-octene.

While the present invention has been illustrated and described above in terms of particular apparatus and methods of use, it is apparent that, having the benefit of the teachings herein, equivalent techniques and ingredients may be substituted for those shown, and other changes can be made within the scope of the present invention as defined by the appended claims.

What is claimed as our invention is:
1. A method comprising:
 contacting an oligomerization catalyst system and a feed comprising olefins and a diluent;
 oligomerizing said feed in at least one continuous reactor; and
 withdrawing from said at least one continuous reactor an effluent comprising product olefins having at least four carbon atoms, wherein the effluent comprises the diluent and wherein the diluent comprises 1-butene, 1-dodecene, 1-tetradecene, 1-hexadecene, 1-octadecene, or combinations thereof;
 wherein the oligomerization catalyst system comprises a metal complex activated by a co-catalyst and wherein said metal complex comprises a ligand having chemical structure II:

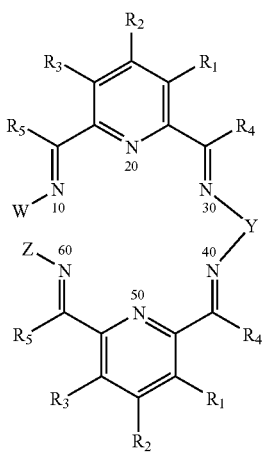

II wherein $R_1$, $R_2$, and $R_3$ are each independently hydrogen, hydrocarbyl, substituted hydrocarbyl, or an inert functional group;

$R_4$ and $R_5$ are each independently hydrogen, hydrocarbyl, an inert functional group, or substituted hydrocarbyl; and Y is a structural bridge between two halves of the structure and is selected from the following group:

(A) Y is cyclohexane and W, and Z are each independently hydrogen, hydrocarbyl, an inert functional group, or substituted hydrocarbyl having from about 0 to about 30 carbon atoms;

(B) Y, W and Z are selected to provide the following structure:

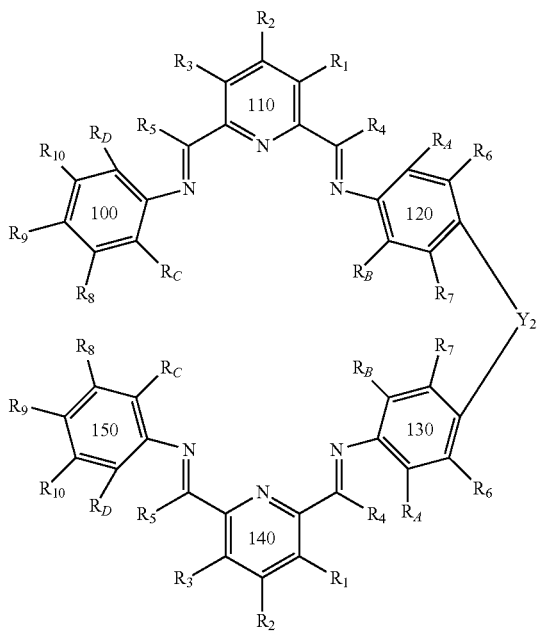

wherein $R_6$, $R_7$, $R_8$, $R_9$, and $R_{10}$ are each independently hydrogen, hydrocarbyl, an inert functional group, or substituted hydrocarbyl;

$R_A$, $R_B$, $R_C$, and $R_D$ are each independently hydrogen, fluorine, an inert functional group, a primary carbon group, a secondary carbon group, or a tertiary carbon group;

$Y_2$ is a structural bridge between two halves of the structure, and more particularly may be a bond, a hydrocarbyl group comprising from about 2 to about 20 carbon atoms, ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring;

(C) Y, W and Z are selected to provide the following structure:

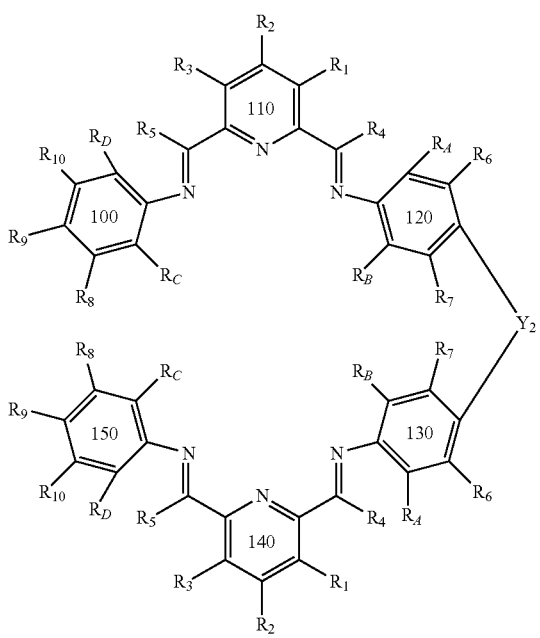

wherein $R_6$, $R_7$, $R_8$, $R_9$, and $R_{10}$ are each independently hydrogen, hydrocarbyl, an inert functional group, or substituted hydrocarbyl;

$R_A$, $R_B$, $R_C$, and $R_D$ are each independently hydrogen, fluorine, an inert functional group, a primary carbon group, a secondary carbon group, or a tertiary carbon group;

$Y_2$ is a structural bridge between two halves of the structure, and more particularly may be a bond, a hydrocarbyl group comprising from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring; and wherein one of the following conditions is satisfied:

(i) when $R_A$ and $R_B$ are hydrogen, then $R_C$ and $R_D$ are independently methyl, ethyl, propyl, or isopropyl;
(ii) when $R_C$ and $R_D$ are hydrogen, then $R_A$ and $R_B$ are independently methyl, ethyl, propyl, or isopropyl;
(iii) when $R_A$ and $R_D$ are hydrogen, then $R_B$ and $R_C$ are independently methyl, ethyl, propyl, or isopropyl;
(iv) when $R_A$ is a primary carbon group, then none, one, or two of $R_B$, $R_C$, and $R_D$ are primary carbon groups, secondary carbon groups, phenyl, substituted phenyl, or inert functional groups, and the remainder of $R_B$, $R_C$, and $R_D$ are hydrogen or fluorine;
(v) when $R_A$ is a secondary carbon group, then none, one, or two of $R_B$, $R_C$ and $R_D$ are primary carbon groups, secondary carbon groups, phenyl, substituted phenyl, or inert functional groups, and the remainder of $R_B$, $R_C$, and $R_D$ are hydrogen or fluorine;
(vi) when $R_A$ is a tertiary carbon group, then none or one of $R_B$, $R_C$, and $R_D$ are tertiary, phenyl, or substituted phenyl, and the remainder are hydrogen or fluorine;
(vii) when $R_C$ is a primary carbon group, then none, one, or two of $R_A$, $R_B$, and $R_D$ are primary carbon groups, secondary carbon groups, phenyl, substituted phenyl, or inert functional groups, and the remainder of $R_A$, $R_B$, and $R_D$ are hydrogen or fluorine;
(viii) when $R_C$ is a secondary carbon group, then none, one, or two of $R_A$, $R_B$ and $R_D$ are primary carbon groups, secondary carbon groups, phenyl, substituted phenyl, or inert functional groups, and the remainder of $R_A$, $R_B$, and $R_D$ are hydrogen or fluorine; or
(ix) when $R_C$ is a tertiary carbon group, then none or one of $R_A$, $R_B$, and $R_D$ are tertiary, phenyl, or substituted phenyl, and the remainder of $R_A$, $R_B$, and $R_D$ are hydrogen or fluorine;

and wherein said metal complex further comprises iron or cobalt, or combinations thereof; and wherein oligomerization to product olefins having at least four carbon atoms comprises a single pass conversion of ethylene of at least about 40 weight percent.

2. The method of claim 1, wherein the single pass conversion of ethylene is at least about 65 weight percent.

3. The method of claim 1, wherein product olefins having twelve carbon atoms comprise at least about 95 weight percent 1-dodecene.

4. The method of claim 1, wherein the effluent comprises at least about 40 weight percent product olefins having at least four carbon atoms.

5. The method of claim 1, wherein said product olefins comprise at least about 80 weight percent linear 1-alkenes.

6. The method of claim 1, wherein said product olefins comprise at least about 20 weight percent alpha olefins having from about 8 to about 20 carbon atoms.

7. The method of claim 1, wherein said oligomerization catalyst system comprises a metal alkyl or metal hydride species.

8. The method of claim 7, wherein said metal alkyl or metal hydride species comprises one or more Lewis acids; a combination of one or more Lewis acids and one or more alkylating agents; one or more alkyl aluminum compounds; one or more alkyl aluminoxanes; methyl aluminoxane (MAO); modified MAO; tri-alkyl aluminum; diethylaluminum chloride (DEAC); or combinations thereof.

9. The method of claim 1, wherein said oligomerization catalyst system comprises triethylaluminum (TEA), trimethylaluminum (TMA), tri-isobutyl aluminum (TIBA), tributyl aluminum, or combinations thereof.

10. The method of claim 1, wherein said oligomerization catalyst system is activated in the absence of ethylene.

11. The method of claim 1, wherein said oligomerization catalyst system comprises a selective 1-hexene (S1H) catalyst.

12. The method of claim 11, wherein said oligomerization catalyst system comprises chromium.

13. The method of claim 1, wherein said at least one continuous reactor comprises a loop reactor, tubular reactor, continuous stirred tank reactor, or combinations thereof.

14. The method of claim 1, wherein said at least one continuous reactor comprises a loop reactor and fluid flow in said loop reactor comprises a Reynolds number of from about 200,000 to about 700,000.

15. The method of claim 1, wherein said at least one continuous reactor comprises a tubular reactor and fluid flow in said tubular reactor comprises a Reynolds number of from about 300,000 to about 2,000,000.

16. The method of claim 1, wherein at steady state the contents of said reactor are not turbid.

17. The method of claim 1, wherein the effluent comprises a diluent and wherein said diluent comprising aliphatics, non-aliphatics, aromatics, saturated compounds having from 4 to 8 carbon atoms, or combinations thereof.

18. The method of claim 1, wherein the effluent comprises a diluent and wherein said diluent comprises an aromatic compound having from about 6 to about 30 carbon atoms, or combinations thereof.

19. The method of claim 1, wherein the effluent comprises a diluent and wherein said diluent comprises cyclohexane, benzene, toluene, xylene, ethylbenzene, or combinations thereof.

20. The method of claim 1, wherein the effluent comprises a diluent and wherein said diluent comprises olefins having from about 4 to about 30 carbon atoms, or combinations thereof.

21. The method of claim 1, further comprising manipulating product olefin distribution by modifying a pressure of the reactor.

22. The method of claim 1, further comprising injecting said feed and said catalyst system into said reactor at more than one point along the length of said reactor wherein said reactor is a tubular reactor.

23. The method of claim 1, further comprising cooling said reactor with a coolant more volatile than water.

24. The method of claim 1, further comprising cooling said reactor with a coolant, wherein said coolant comprises butane, isobutane, isopentane, or combinations thereof.

25. The method of claim 1, wherein said reactor comprises a temperature of from about 40 to about 150 degrees Celsius.

26. A method comprising:
contacting an oligomerization catalyst system and a feed comprising olefins and a diluent;
oligomerizing said feed in at least one continuous reactor; and
withdrawing from said at least one continuous reactor an effluent comprising product olefins having at least four carbon atoms, wherein the effluent comprises the diluent and wherein the diluent comprises 1-butene, 1-dodecene, 1-tetradecene, 1-hexadecene, 1-octadecene, or combinations thereof;
wherein oligomerization to product olefins having at least four carbon atoms comprises a single pass conversion of ethylene of at least about 65 weight percent;
wherein product olefins having twelve carbon atoms comprise at least about 95 weight percent 1-dodecene, and
wherein the catalyst system comprises a metal complex activated by a co-catalyst and wherein said metal complex comprises a ligand having chemical structure II:

II

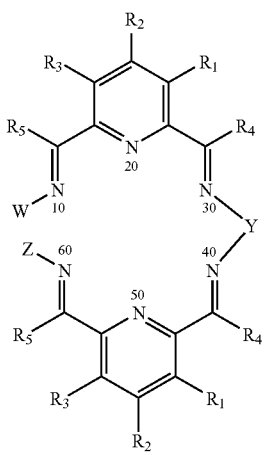

wherein $R_1$, $R_2$, and $R_3$ are each independently hydrogen, hydrocarbyl, substituted hydrocarbyl, or an inert functional group;

$R_4$ and $R_5$ are each independently hydrogen, hydrocarbyl, an inert functional group, or substituted hydrocarbyl; and Y is a structural bridge between two halves of the structure and is selected from the following group:

(A) Y is cyclohexane and W, and Z are each independently hydrogen, hydrocarbyl, an inert functional group, or substituted hydrocarbyl having from about 0 to about 30 carbon atoms:

(B) Y, W and Z are selected to provide the following structure:

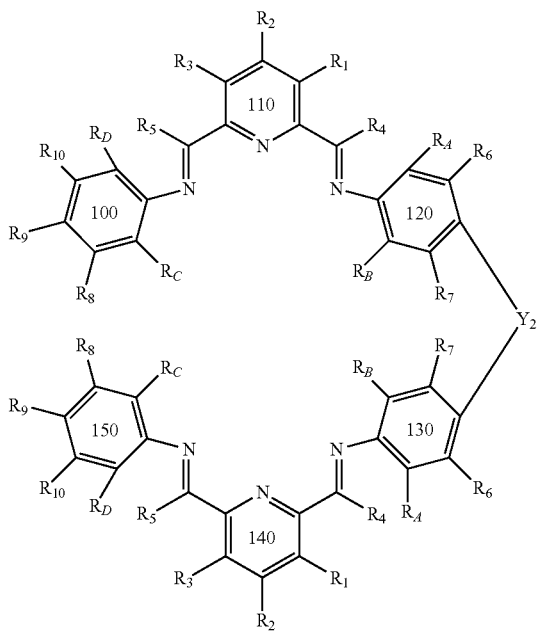

wherein $R_6$, $R_7$, $R_8$, $R_9$, and $R_{10}$ are each independently hydrogen, hydrocarbyl, an inert functional group, or substituted hydrocarbyl;

$R_A$, $R_B$, $R_C$, and $R_D$ are each independently hydrogen, fluorine, an inert functional group, a primary carbon group, a secondary carbon group, or a tertiary carbon group;

$Y_2$ is a structural bridge between two halves of the structure, and more particularly may be a bond, a hydrocarbyl group comprising from about 2 to about 20 carbon atoms, ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring;-

(C) Y, W and Z are selected to provide the following structure:

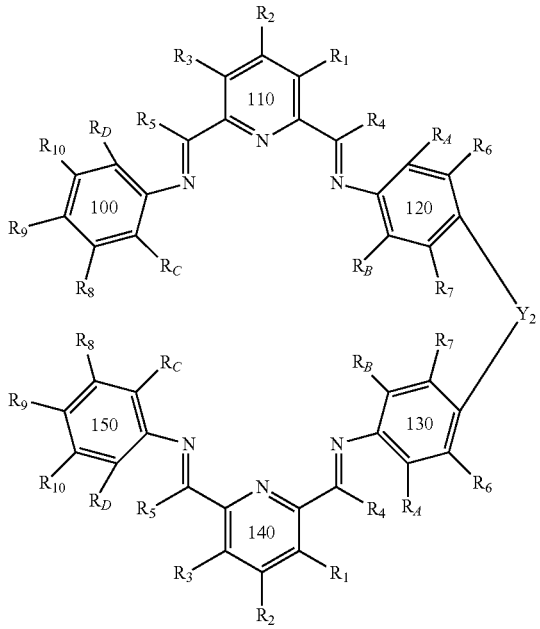

wherein $R_6$, $R_7$, $R_8$, $R_9$, and $R_{10}$ are each independently hydrogen, hydrocarbyl, an inert functional group, or substituted hydrocarbyl;

$R_A$, $R_B$, $R_C$, and $R_D$ are each independently hydrogen, fluorine, an inert functional group, a primary carbon group, a secondary carbon group, or a tertiary carbon group;

$Y_2$ is a structural bridge between two halves of the structure, and more particularly may be a bond, a hydrocarbyl group comprising from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring; and wherein one of the following conditions is satisfied:

(i) when $R_A$ and $R_B$ are hydrogen, then $R_C$ and $R_D$ are independently methyl, ethyl, propyl, or isopropyl;

(ii) when $R_C$ and $R_D$ are hydrogen, then $R_A$ and $R_B$ are independently methyl, ethyl, propyl, or isopropyl;

(iii) when $R_A$ and $R_D$ are hydrogen, then $R_B$ and $R_C$ are independently methyl, ethyl, propyl, or isopropyl;

(iv) when $R_A$ is a primary carbon group, then none, one, or two of $R_B$, $R_C$, and $R_D$ are primary carbon groups, secondary carbon groups, phenyl, substituted phenyl, or inert functional groups, and the remainder of $R_B$, $R_C$, and $R_D$ are hydrogen or fluorine;

(v) when $R_A$ is a secondary carbon group, then none, one, or two of $R_B$, $R_C$ and $R_D$ are primary carbon groups, secondary carbon groups, phenyl, substituted phenyl, or inert functional groups, and the remainder of $R_B$, $R_C$, and $R_D$ are hydrogen or fluorine;

(vi) when $R_A$ is a tertiary carbon group, then none or one of $R_B$, $R_C$, and $R_D$ are tertiary, phenyl, or substituted phenyl, and the remainder are hydrogen or fluorine;

(vii) when $R_C$ is a primary carbon group, then none, one, or two of $R_A$, $R_B$, and $R_D$ are primary carbon groups, secondary carbon groups, phenyl, substituted phenyl, or inert functional groups, and the remainder of $R_A$, $R_B$, and $R_D$ are hydrogen or fluorine;

(viii) when $R_C$ is a secondary carbon group, then none, one, or two of $R_A$, $R_B$ and $R_D$ are primary carbon groups, secondary carbon groups, phenyl, substituted phenyl, or inert functional groups, and the remainder of $R_A$, $R_B$, and $R_D$ are hydrogen or fluorine; or (ix) when $R_C$ is a tertiary carbon group, then none or one of $R_A$, $R_B$, and $R_D$ are tertiary, phenyl, or substituted phenyl, and the remainder of $R_A$, $R_B$, and $R_D$ are hydrogen or fluorine.

27. The method of claim 1 wherein the ligand has a chemical structure:

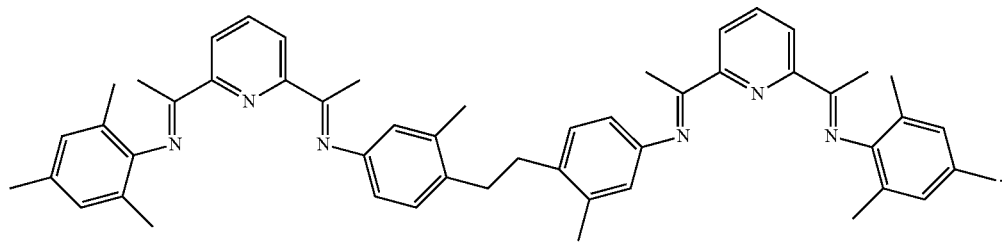

28. The method of claim 1 wherein the ligand has a chemical structure:
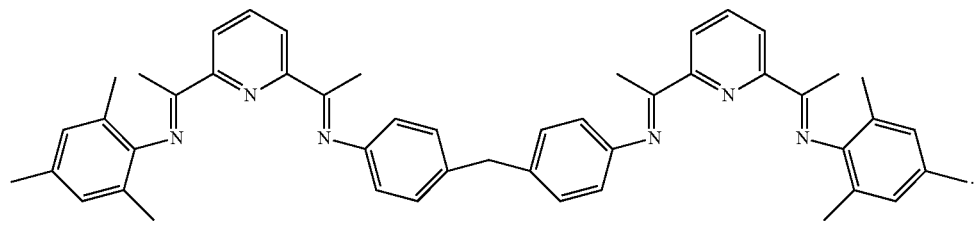
29. The method of claim 1 wherein the ligand has a chemical structure:
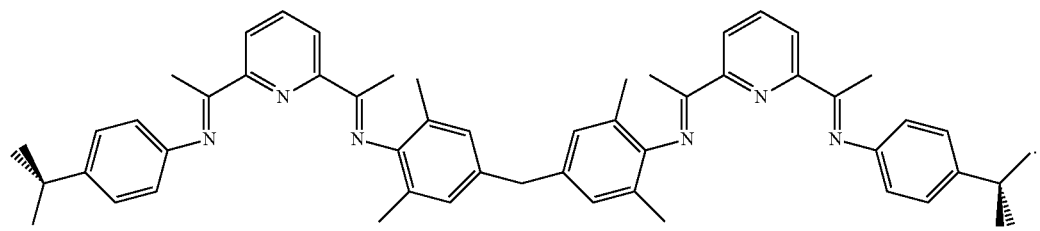
30. The method of claim 1 wherein the metal complex has a chemical structure:
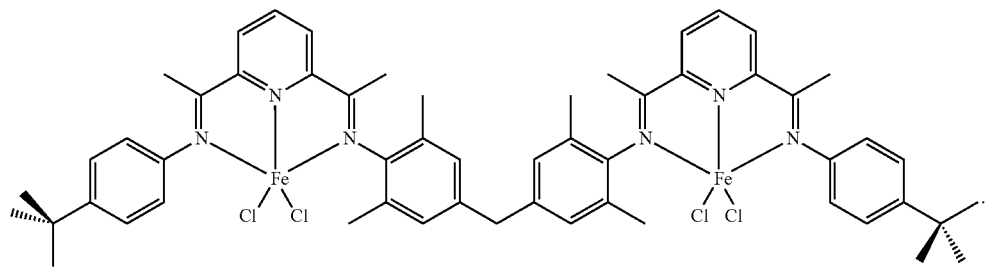
31. The method of claim 26 wherein the ligand has a chemical structure:
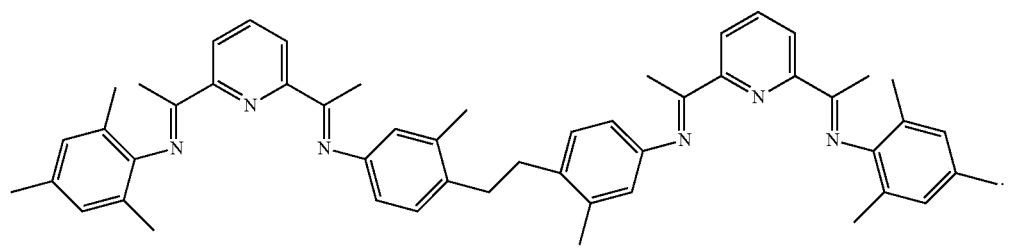

32. The method of claim 26 wherein the ligand has a chemical structure:
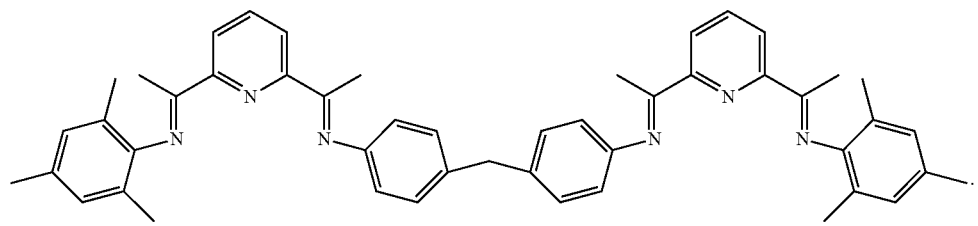
33. The method of claim 26 wherein the ligand has a chemical structure:
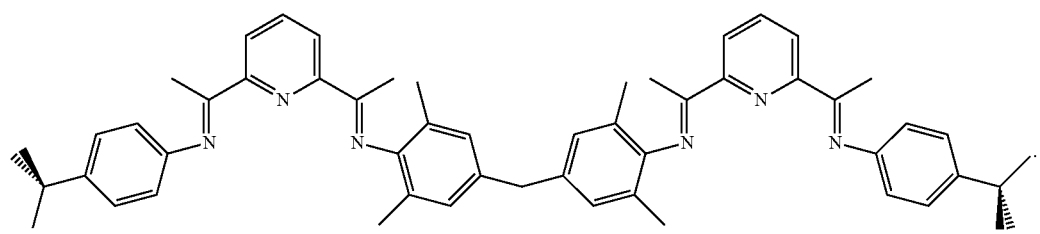
34. The method of claim 26 wherein the metal complex has a chemical structure:
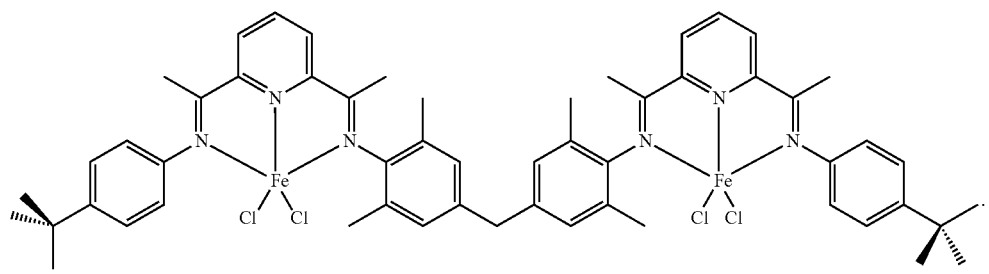
* * * * *